US011076752B2

(12) United States Patent
Ohara

(10) Patent No.: US 11,076,752 B2
(45) Date of Patent: Aug. 3, 2021

(54) ENDOSCOPE LIGHT SOURCE SYSTEM

(71) Applicant: OLYMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 777 days.

(21) Appl. No.: 15/596,076

(22) Filed: May 16, 2017

(65) Prior Publication Data

US 2017/0245745 A1 Aug. 31, 2017

Related U.S. Application Data

(63) Continuation of application No. PCT/JP2014/080509, filed on Nov. 18, 2014.

(51) Int. Cl.
*A61B 1/06* (2006.01)
*A61B 1/00* (2006.01)
*A61B 1/07* (2006.01)

(52) U.S. Cl.
CPC ........ *A61B 1/0661* (2013.01); *A61B 1/00126* (2013.01); *A61B 1/063* (2013.01);
(Continued)

(58) Field of Classification Search
CPC ... A61B 1/0661; A61B 1/0669; A61B 1/0676; A61B 1/0684; A61B 1/04; A61B 1/041;
(Continued)

(56) References Cited

U.S. PATENT DOCUMENTS

2004/0210112 A1* 10/2004 Ota ...................... A61B 1/0684
600/180
2005/0267333 A1* 12/2005 Hino .................. A61B 1/00114
600/132
(Continued)

FOREIGN PATENT DOCUMENTS

JP          S63-68127 A    3/1988
JP          H05-053064 A   3/1993
(Continued)

OTHER PUBLICATIONS

International Search Report dated Mar. 10, 2015 issued in PCT/JP2014/080509.
(Continued)

*Primary Examiner* — Ryan N Henderson
(74) *Attorney, Agent, or Firm* — Scully, Scott, Murphy & Presser, P.C.

(57) ABSTRACT

An endoscope light source system includes a light source module, an insertion module and a light guide path. The light source system further includes a light connector which is provided on the light guide path and optically connects an auxiliary light guide path to the light guide path, such that auxiliary light is guided to the light guide path from the auxiliary light guide path which guides the auxiliary light; and an irradiation module which emits at least one of light-source light which is guided by the light guide path and the auxiliary light which is guided by the light guide path, to an outside of an endoscope as illumination light, and radiates the illumination light to a to-be-illuminated part.

16 Claims, 12 Drawing Sheets

(52) U.S. Cl.
CPC ......... *A61B 1/0638* (2013.01); *A61B 1/0653* (2013.01); *A61B 1/0669* (2013.01); *A61B 1/07* (2013.01)

(58) Field of Classification Search
CPC ......... A61B 1/042; A61B 1/043; A61B 1/045; A61B 1/05; A61B 1/051; A61B 1/053; A61B 1/055; A61B 1/06; A61B 1/0607; A61B 1/0615; A61B 1/0623; A61B 1/063; A61B 1/0638; A61B 1/0646; A61B 1/0653; A61B 1/07; A61B 1/0063; A61B 1/00165; A61B 1/00167; A61B 1/0017; A61B 1/00172; A61B 1/00174; A61B 1/00177; A61B 1/00179; A61B 1/00181; A61B 1/00183; A61B 1/00186; A61B 1/00188; A61B 1/0019; A61B 1/00193; A61B 1/00195; A61B 1/00197; A61B 1/002; G02B 23/24; G02B 23/2407; G02B 23/2415; G02B 23/2423; G02B 23/243; G02B 23/2438; G02B 23/2446; G02B 23/2453; G02B 23/2461; G02B 23/2469
See application file for complete search history.

(56) References Cited

U.S. PATENT DOCUMENTS

| | | | | |
|---|---|---|---|---|
| 2009/0030275 | A1* | 1/2009 | Nicolaou | G06T 5/008 600/109 |
| 2010/0067002 | A1* | 3/2010 | Ishii | A61B 1/0638 356/317 |
| 2010/0125165 | A1* | 5/2010 | Torn | A61B 1/00045 600/106 |
| 2011/0077465 | A1* | 3/2011 | Mizuyoshi | A61B 1/0607 600/180 |
| 2011/0164249 | A1* | 7/2011 | Innami | G01N 21/645 356/326 |
| 2011/0213252 | A1* | 9/2011 | Fulghum | A61B 1/00009 600/476 |
| 2011/0234782 | A1* | 9/2011 | Ehrhardt | A61B 1/063 348/68 |
| 2011/0235324 | A1* | 9/2011 | Irion | A61B 1/0638 362/235 |
| 2012/0123205 | A1* | 5/2012 | Nie | A61B 1/00174 600/109 |
| 2012/0302847 | A1* | 11/2012 | Ozawa | A61B 1/0638 600/339 |
| 2014/0286038 | A1* | 9/2014 | Ito | G02B 6/0008 362/554 |

FOREIGN PATENT DOCUMENTS

| | | |
|---|---|---|
| JP | H09-292575 A | 11/1997 |
| JP | 2000-310739 A | 11/2000 |
| JP | 2003-051765 A | 2/2003 |
| JP | 2009-189473 A | 8/2009 |
| JP | 2011-147757 A | 8/2011 |
| JP | 2012-217483 A | 11/2012 |
| JP | 5350643 B2 | 11/2013 |
| JP | 2014-025981 A | 2/2014 |
| JP | 2014-117324 A | 6/2014 |

OTHER PUBLICATIONS

English Abstract only of JP 2009-189473 A, dated Aug. 27, 2009.
Japanese Office Action dated Feb. 20, 2018 in Japanese Patent Application No. 2016-559725.
English translation of International Preliminary Report on Patentability dated Jun. 1, 2017 together with the Written Opinion received in related International Application No. PCT/JP2014/080509.
Chinese Office Action dated Jan. 2, 2018 in Chinese Patent Application No. 201480083521.6.

* cited by examiner

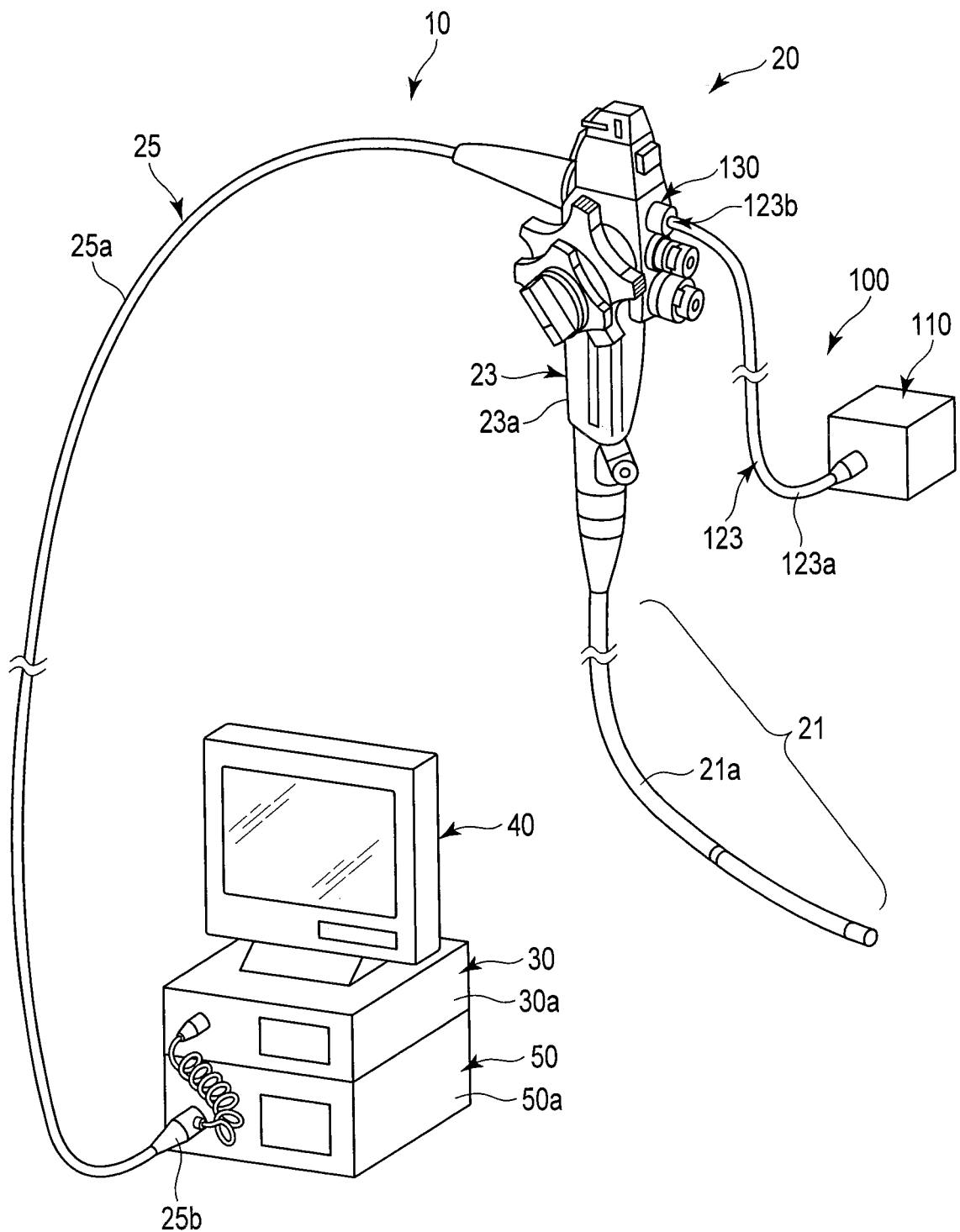
F I G. 1

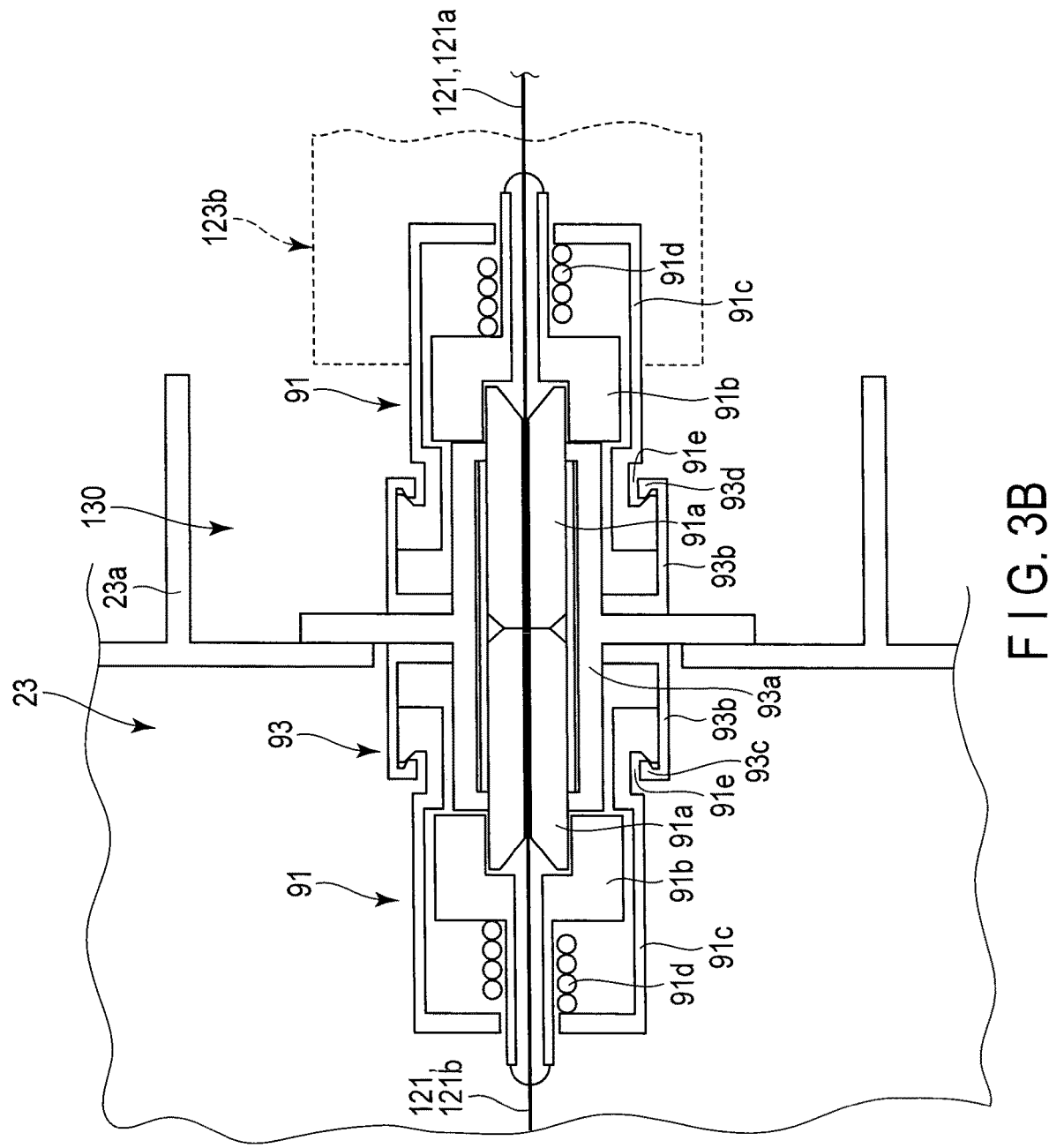
F I G. 3B

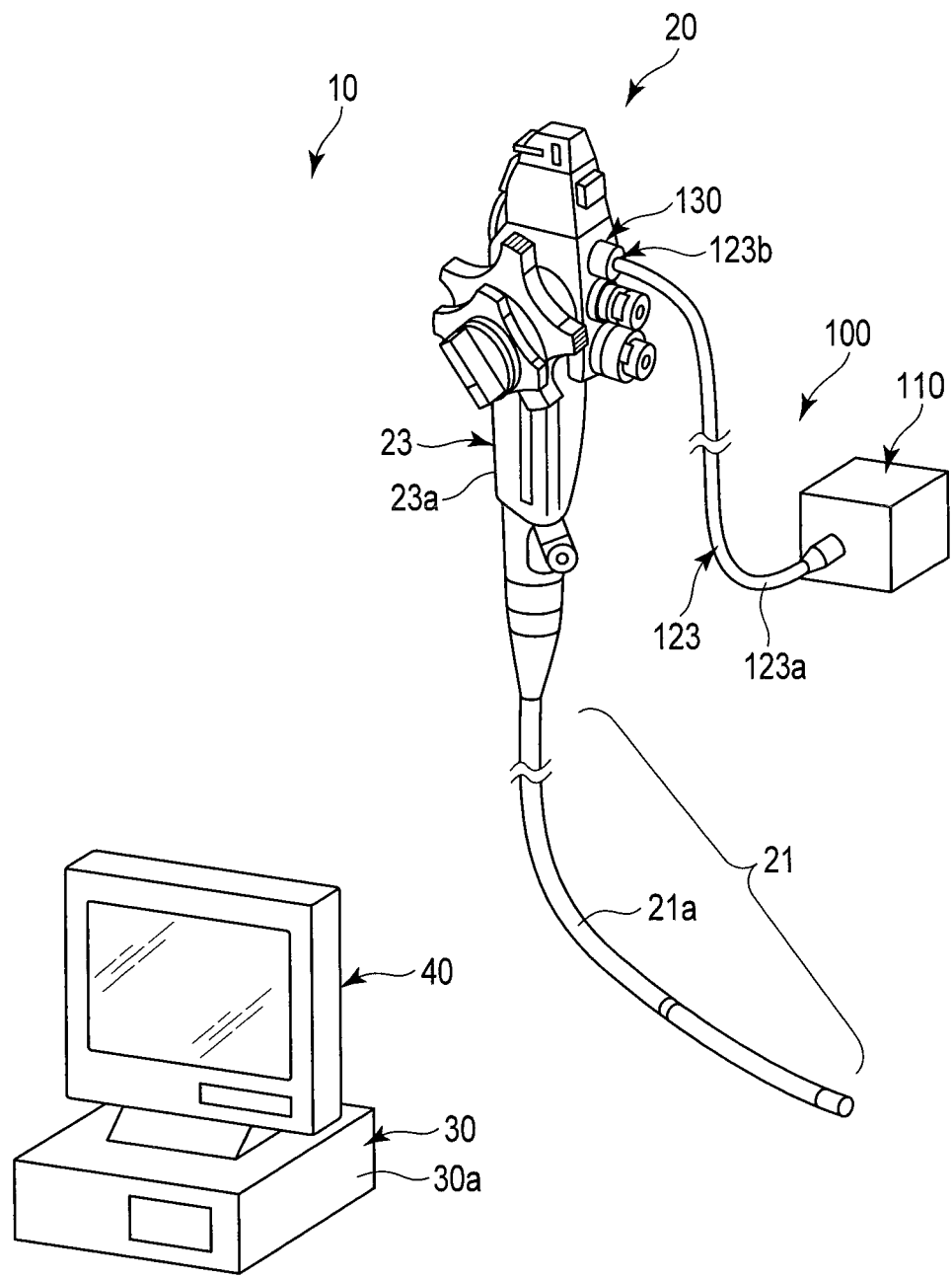
F I G. 4A

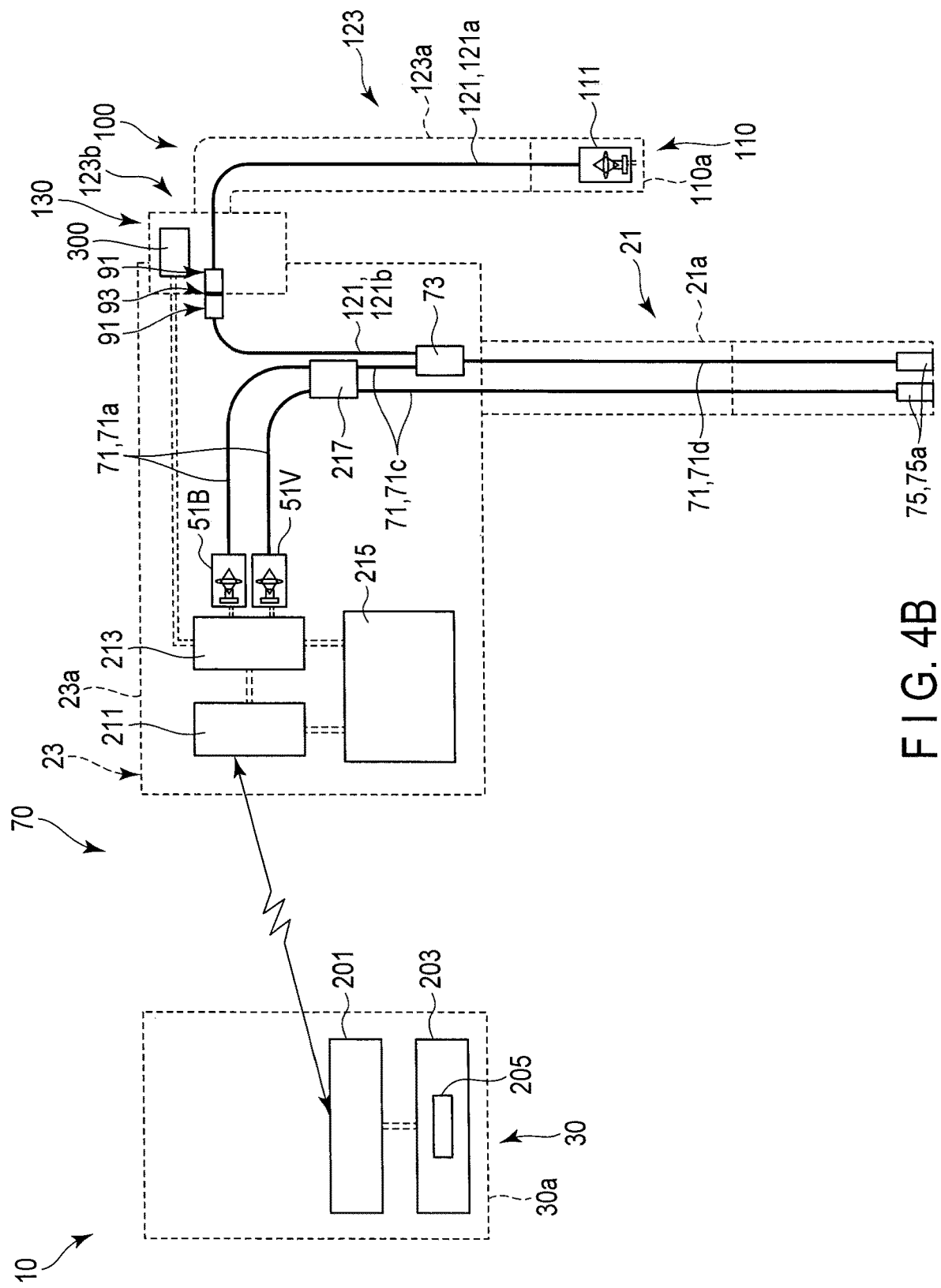
F I G. 4B

ENDOSCOPE LIGHT SOURCE SYSTEM

CROSS-REFERENCE TO RELATED APPLICATIONS

This application is a Continuation application of PCT Application No. PCT/JP2014/080509, filed Nov. 18, 2014, the entire contents of all of which are incorporated herein by reference.

BACKGROUND OF THE INVENTION

1. Field of the Invention

The present invention relates to an endoscope light source system.

2. Description of the Related Art

For example, Japanese Patent No. 5350643 discloses an endoscope light source system including a single optical fiber which functions as a light guide path that guides light-source light. In this endoscope light source system, a laser beam that is the light-source light is emitted from a laser light source and is guided by the single optical fiber in an inside of an endoscope. In addition, the laser beam is wavelength-converted by a phosphor provided at a distal end portion of an insertion module of the endoscope, and the wave-length-converted laser beam is emitted to an outside as illumination light.

BRIEF SUMMARY OF THE INVENTION

According to an embodiment of the present invention, an endoscope light source system includes a light source module including a light source which emits light-source light; an insertion module which is provided in an endoscope connected to the light source module and is inserted in a lumen; a light guide path which is provided in the light source module and the endoscope including the insertion module, is optically connected to the light source, and guides the light-source light emitted from the light source; a light connector which is provided on the light guide path and optically connects an auxiliary light guide path to the light guide path, such that auxiliary light is guided to the light guide path from the auxiliary light guide path which guides the auxiliary light; and an irradiation module which is optically connected to the light guide path, emits at least one of the light-source light which is guided by the light guide path and the auxiliary light which is guided by the light guide path, to an outside of the endoscope as illumination light, and radiates the illumination light to a to-be-illuminated part.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic perspective view of an endoscope system according to a first embodiment of the present invention.

FIG. 3B is a view for describing the method of optically connecting the light guide member provided on the auxiliary connector side and the light guide member provided on the guide mouth portion side.

FIG. 4A is a schematic perspective view of an endoscope system according to a second embodiment of the present invention.

FIG. 4B is a schematic view of an endoscope light source system according to the second embodiment.

DETAILED DESCRIPTION OF THE INVENTION

Figure 2A:
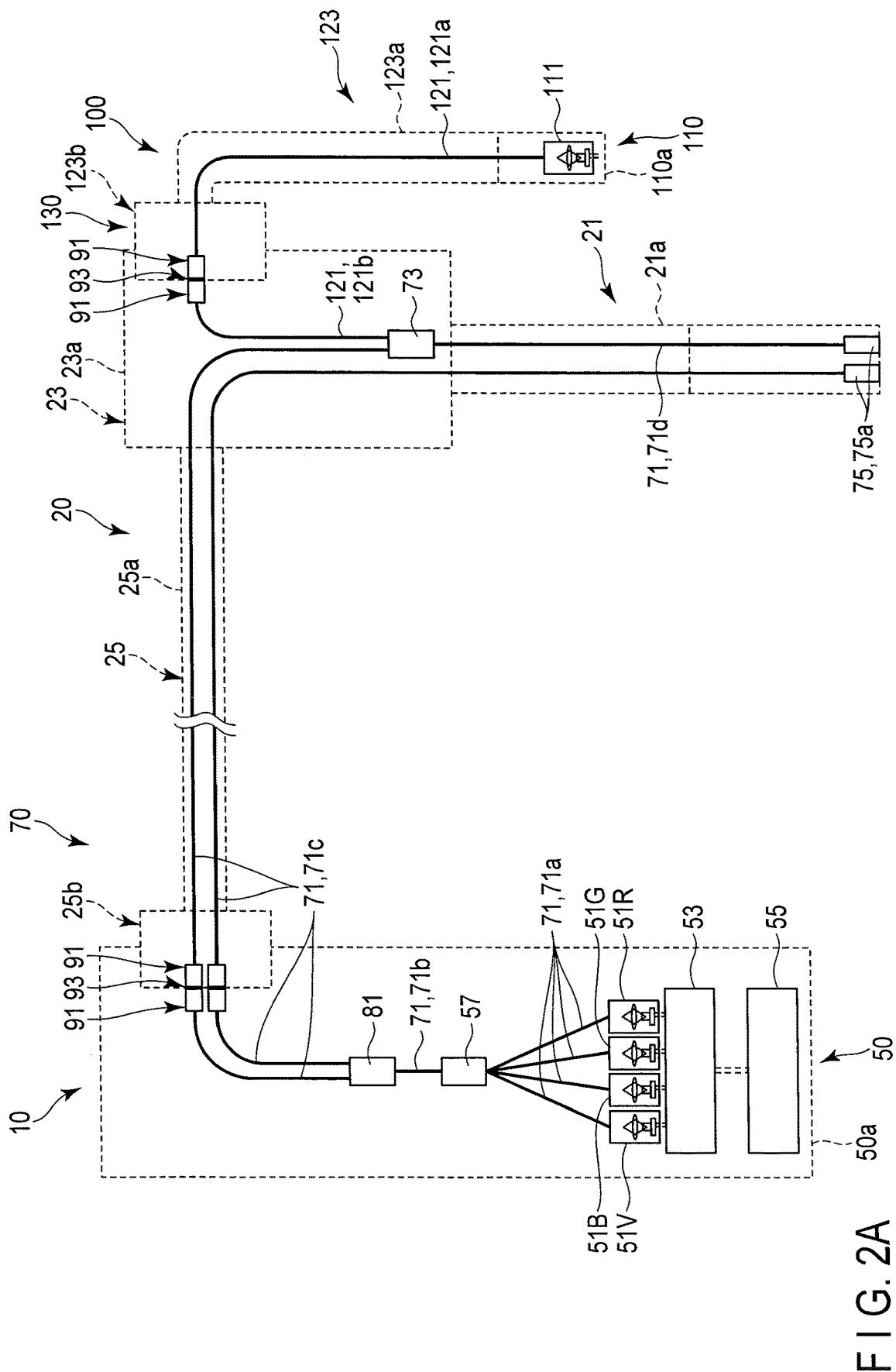
FIG. 2A is a schematic view of an endoscope light source system according to the first embodiment in a case in which a light separator is provided in a light source module.

Hereinafter, embodiments of the present invention will be described in detail with reference to the accompanying drawings. Incidentally, in some of the drawings, depiction of some members is omitted for the purpose of clearer illustration.

First Embodiment

A first embodiment will be described with reference to FIG. 1, FIG. 2A, FIG. 2B, FIG. 2C, FIG. 2D, FIG. 2E, FIG. 3A and FIG. 3B. In some of the drawings, depiction of some members is omitted for the purpose of clearer illustration.

An endoscope system 10 as illustrated in FIG. 1 is installed, for example, in an examination room or an operating room. The endoscope system 10 includes an endoscope 20 which captures an image of, for example, an inside of a lumen of a patient or the like, and an image processor (image processing device) 30 which processes the image of the inside of the lumen, the image being captured by an imager (imaging unit ((for example, CCD) not shown)) of the endoscope 20. The endoscope system 10 further includes a display (display portion) 40 which is connected to the image processor 30 and displays the image which was captured by the imager and processed by the image processor 30, and a light source module 50 which emits light-source light for illumination light that is emitted from the endoscope 20. The display 40 has a monitor, for example.

The endoscope 20 as illustrated in FIG. 1 functions, for example, as an insertion device which is inserted into the lumen. The endoscope 20 may be a forward-viewing endoscope 20 or a side-viewing endoscope 20.

The endoscope 20 of the present embodiment is described as being, for example, an endoscope 20 for medical use, but the restriction to this is unnecessary. The endoscope 20 may also preferably be an endoscope for industrial use, which is inserted in a cavity of an industrial product, such as a pipe, or an insertion instrument, such as a catheter, which includes only an illumination optical system.

As illustrated in FIG. 1, the endoscope 20 includes an insertion module 21 which is hollow and elongated and is inserted into, for example, the lumen; an operation portion 23 which is coupled to a proximal end portion of the insertion module 21 and operates the endoscope 20; and a universal cord 25 which is connected to the operation portion 23 and is made to extend from a side surface of the operation portion 23.

As illustrated in FIG. 1, the insertion module 21 includes a housing (housing portion) 21a which is provided on at least a part of the insertion module 21 and has flexibility. The housing 21a includes, for example, a flexible tube (flexible tube portion).

As illustrated in FIG. 1, the operation portion 23 includes a housing (housing portion) 23a having desired rigidity.

As illustrated in FIG. 1, the universal cord 25 includes a housing (housing portion) 25a which has flexibility and has desired rigidity. The universal cord 25 includes a connector (connection portion) 25b which is attachable/detachable to/from the image processor 30 and light source module 50. The connector 25b detachably connects the light source module 50 and endoscope 20 to each other. As illustrated in FIG. 2A, the connector 25b is provided closer to the light source module 50 side than a guide mouth portion (guide mouth) 130 and a light connector (light connection portion) 73, which will be described later. The connector 25b connects the endoscope 20 to the image processor 30 and light source module 50. The connector 25b is provided in order to enable data transmission/reception between the endoscope 20 and image processor 30 and between the endoscope 20 and light source module 50.

The image processor 30 includes a housing (housing portion) 30a having desired rigidity.

As illustrated in FIG. 1, the image processor 30 and light source module 50 are electrically connected to each other. The image processor 30 and light source module 50 are detachably connected to the endoscope 20 via the connector 25b.

As illustrated in FIG. 1, the light source module 50 includes a housing (housing portion) 50a having desired rigidity. The light source module 50 is a separate body from the endoscope 20, and is provided an outside of the endoscope 20.

As illustrated in FIG. 2A, the endoscope system 10 further includes an endoscope light source system 70 (hereinafter referred to as "light source system 70") which emits illumination light to the outside from the distal end portion of the insertion module 21.

As illustrated in FIG. 2A, the light source system 70 includes the above-described light source module 50 including a light source which emits light-source light, and the above-described insertion module 21 which is provided in the endoscope 20 connected to the light source module 50 and is inserted in the lumen.

The light source system 70 further includes a light guide path 71 which is provided in the light source module 50 and the endoscope 20 including the insertion module 21, is optically connected to the light source, and guides the light-source light emitted from the light source. The light source system 70 further includes the light connector 73 which is provided on the light guide path 71 and optically connects an auxiliary light guide path 121 to the light guide path 71, such that auxiliary light is guided to the light guide path 71 from the auxiliary light guide path 121 which guides the auxiliary light.

The light guide system 70 further includes an irradiation module 75 which is optically connected to the light guide path 71, emits at least one of the light-source light which is guided by the light guide path 71 and the auxiliary light which is guided by the light guide path 71, to the outside of the endoscope 20 as illumination light, and radiates the illumination light to a to-be-illuminated part.

As illustrated in FIG. 2A, a plurality of the light sources are provided. In the description below, the respective light sources are referred to as light sources 51V, 51B, 51G and 51R. The light sources 51V, 51B, 51G and 51R are mounted on a control board (not shown) which forms a controller (control portion) 53 that controls the light sources 51V, 51B, 51G and 51R individually, and the controller 53 is electrically connected to a controller (control portion) 55. The controller 55 controls the entirety of the endoscope system 10 including the endoscope 20, display 40 and light source module 50. The controller 53 and controller 55 have, for example, a hardware circuitry including ASIC.

The light sources 51V, 51B, 51G and 51R emit light-source lights having mutually optically different wavelengths. The light sources 51V, 51B, 51G and 51R emit the light-source lights having high coherence, such as laser beams.

The light source 51V includes, for example, a laser diode which emits a violet laser beam. A central wavelength of the laser beam is, for example, 405 nm.

The light source 51B includes, for example, a laser diode which emits a blue laser beam. A central wavelength of the laser beam is, for example, 445 nm.

The light source 51G includes, for example, a laser diode which emits a green laser beam. A central wavelength of the laser beam is, for example, 510 nm.

The light source 51R includes, for example, a laser diode which emits a red laser beam. A central wavelength of the laser beam is, for example, 630 nm.

Each of the light sources 51V, 51B, 51G and 51R is optically connected to a light coupler (light coupling portion) 57 (to be described later) via a light focusing lens (not shown) and a single light guide member (single light guide) 71a. The light guide member 71a includes, for example, an optical fiber. A plurality of light-source lights, which are emitted from the light sources 51V, 51B, 51G and 51R, are focused on the single light guide members 71a by the light focusing lenses (not shown). Then, the light-source lights are guided to the light coupler 57 by the light guide members 71a. The light sources 51V, 51B, 51G and 51R, the controllers 53 and 55, the focusing lenses (not shown) and single light guide members 71a are provided in an inside of the housing 50a.

As illustrated in FIG. 2A, the light source system 70 further includes the light coupler 57 which is provided in the inside of the housing 50a of the light source module 50, and couples the plurality of light-source lights, which are emitted from the light sources 51V, 51B, 51G and 51R, into single light.

The light coupler 57 makes the light-source lights, which are guided by the four light guide members 71a, incident on a single light guide member (light guide) 71b. In this manner, in the present embodiment, the light coupler 57 includes four input ports and one output port. The number of input ports is equal to the number of light sources. The number of output ports is not particularly limited. At the input ports, the light guide members 71a include fine optical fibers, and the light guide members 71a are bundled. At the output port, the light guide member 71b includes a thick optical fiber. The thick optical fiber 71b has a greater thickness than the bundled light guide members 71a. The thick optical fiber 71b is fused on the bundled light guide members 71a such that the thick optical fiber 71b is optically connected to the bundled light guide members 71a. The light coupler 57 functions as a light combiner.

As illustrated in FIG. 2A, the light source system 70 further includes a light separator (light separating portion) 81 which is provided in the inside of the housing 50a of the light source module 50, and separates the light-source light, which was coupled by the light coupler 57, into a plurality of light-source lights.

The light separator 81 makes the light-source light, which was guided by the single light guide member 71b, incident on two light guide members (light guides) 71c. In this manner, in the present embodiment, the light separator 81 includes one input port and two output ports. The number of input ports of the light separator 81 is equal to the number of output ports of the light coupler 57. The number of output ports is not limited, if this number is plural. In other words, it should suffice if the number of light guide members 71c is plural. The light separator 81 separates the light-source light, for example, at a desired ratio. In this embodiment, the ratio is, for example, 50:50. It is not necessary that the ratio be equal between the respective output ports. The light separator 81 functions as a light divide portion.

In the structure of the light separator 81, the light guide member 71b and one of the light guide members 71c are one piece. In other words, the light guide member 71b and one of the light guide members 71c function as an identical member, for example, as an identical optical fiber. The other light guide member 71c is fused to this one light guide member, and the fused portion is further melted and drawn. Thereby, light-source light is transferred between the light guide member 71b and the other light guide member 71c. In general, since the fused portion is very fragile, the risk of a fault is very high.

In the present embodiment, the input port of the light separator 81 is optically connected to the output port of the light coupler 57. Thereby, the light-source light, which is input to the light separator 81, is separated into the two light guide members 71c at a ratio of, for example, 50:50.

Figure 2B:
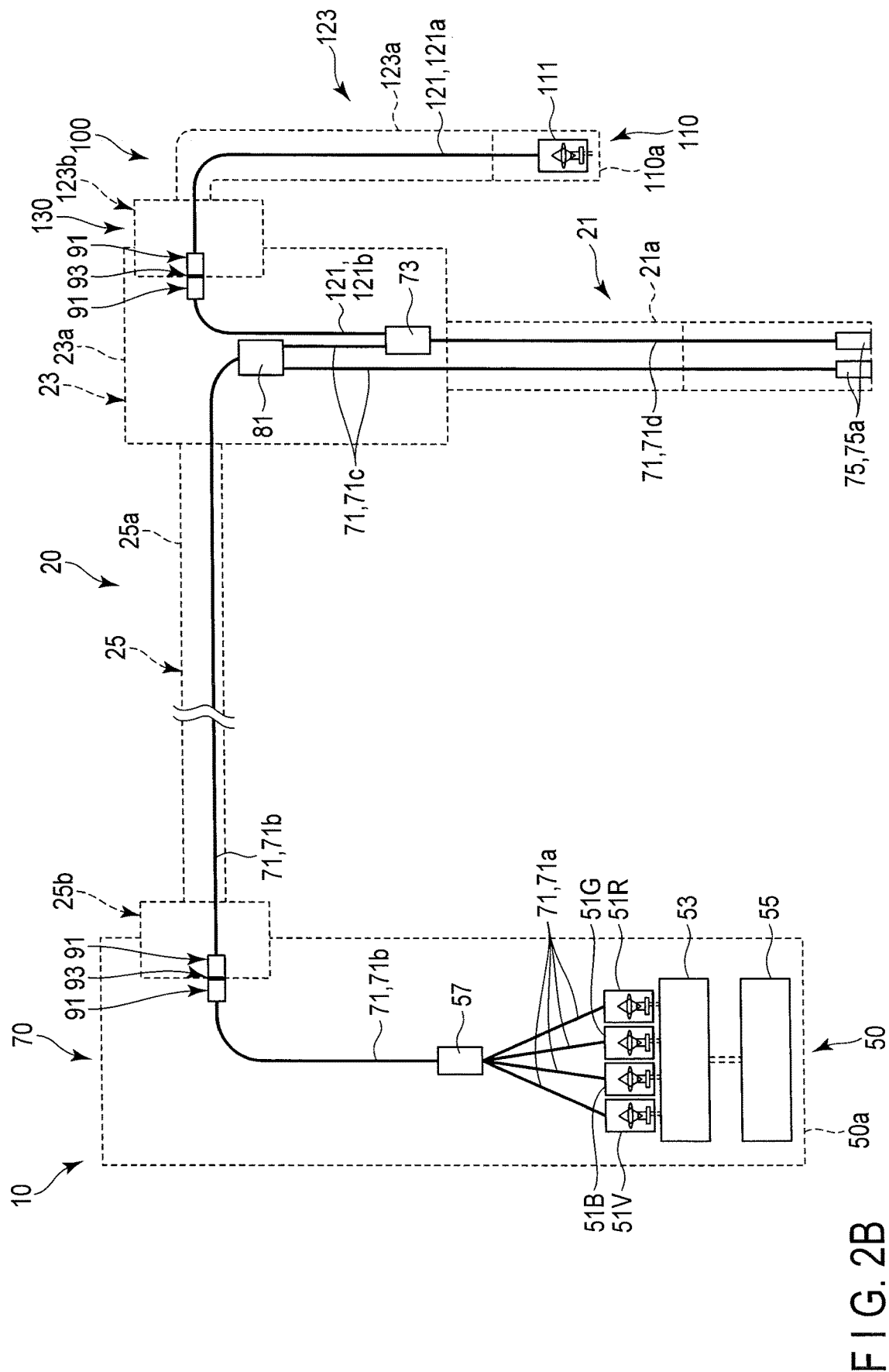
FIG. 2B is a schematic view of the endoscope light source system in a case in which the light separator is provided in an operation portion.

Incidentally, as illustrated in FIG. 2B, the light separator 81 may be provided in an inside of the housing 23a of the operation portion 23 of the endoscope 20. In this manner, it should suffice if the light separator 81 is provided in either the light source module 50 or the endoscope 20.

As illustrated in FIG. 2A, when the light separator 81 is provided in the light source module 50, the light guide member 71b is provided in the inside of the housing 50a of the light source module 50, and the light guide members 71c are provided in the inside of the housing 50a of the light source module 50 and in an inside of the endoscope 20. As illustrated in FIG. 2B, when the light separator 81 is provided in the endoscope 20, the light guide member 71b is provided in the inside of the housing 50a of the light source module 50 and in the inside of the endoscope 20, and the light guide members 71c are provided in the inside of the endoscope 20.

As illustrated in FIG. 2A, the light guide path 71 includes the above-described light guide members 71a which are provided in the light source module 50. The light guide members 71a are optically connected to the light sources and the light coupler 57. The light guide members 71a guide the light-source light from the light sources 51V, 51B, 51G and 51R to the light coupler 57.

The light guide path 71 further includes the light guide member 71b which is provided in the light source module 50 when the light separator 81 is provided in the light source module 50 as illustrated in FIG. 2A, and which is provided in the light source module 50, connector 25b, universal cord 25 and operation portion 23 when the light separator 81 is provided in the operation portion 23 as illustrated in FIG. 2B. The light guide member 71b guides the light-source light from the light coupler 57 to the light separator 81.

The light guide path 71 further includes the light guide members 71c which are provided in the light source module 50, connector 25b, universal cord 25, operation portion 23 and insertion module 21 when the light separator 81 is provided in the light source module 50 as illustrated in FIG. 2A, and which is provided in the operation module 23 and insertion module 21 when the light separator 81 is provided in the operation portion 23 as illustrated in FIG. 2B. At least one light guide member 71c is optically connected to an auxiliary light guide member (auxiliary light guide) 121b (to be described later) of the auxiliary light guide path 121 and is optically connected to the auxiliary connector 73. This light guide member 71c directly guides the light-source light from the light separator 81 to the light connector 73. Of the light guide members 71c excluding the light guide member 71c that is optically connected to the light connector 73, at least one light guide member 71c is optically connected to the irradiation module 75. This light guide member 71c guides the light-source light, which was emitted from the light source module 50, from the light separator 81 to the irradiation module 75. This light guide member 71c may be directly connected to the irradiation module 75, or may be indirectly connected to the irradiation module 75 via a member (not shown, for example, lens).

As illustrated in FIG. 2A, the light guide path 71 further includes a light guide member (light guide) 71d which optically connects the light connector 73 and the irradiation module 75. This light guide member 71d guides the light-source light and auxiliary light from the light connector 73 to the irradiation module 75. Specifically, the light guide member 71d is a sole optical member which is shared by the light-source light and auxiliary light, and is a member having a sole optical function of guiding the light-source light and auxiliary light. The member having the sole optical function is a member which has only one predetermined optical function, and is a member which exhibits only one predetermined optical function, at a predetermined position in the light source system 70. In this case, the optical function means guiding of light-source light and auxiliary light. At a time of the light guide operation of the light guide member, the light guide member guides either light-source light or auxiliary light. Incidentally, the light guide member may guide both the light-source light and the auxiliary light at the same time.

As illustrated in FIG. 2A, the light guide members 71c and 71d, which are provided in the insertion module 21, are provided in the inside of the housing 21a of the insertion module 21.

The light guide members 71a, 71b, 71c and 71d include single optical fibers. In this embodiment, these single optical fibers are provided over the entirety of the light guide path 71, but the restriction to this is unnecessary. It should suffice if single optical fibers are provided on at least a part of the light guide path 71. If single optical fibers are provided on a part of the light guide path 71, a bundle fiber may be provided on the other part of the light guide path 71.

The single optical fibers functioning as the light guide members 71a guide the light-source light which was emitted from the light sources.

In the light guide members 71c, a plurality of single optical fibers are provided, and the optical fibers are single fibers of mutually different systems. In other words, these optical fibers are different members although these optical fibers have the same optical function of light guiding. Moreover, in other words, the light guide members 71c include a plurality of single optical fibers of one kind, respectively. In this case, the light guide members 71c function not as a bundle fiber, but as single optical fibers. The respective single optical fibers of the light guide members 71a, 71b, 71c and 71d are single fibers of mutually different systems, and, in other words, these optical fibers are mutually different members although having the same optical function of light guiding.

As illustrated in FIG. 2A, when the light separator 81 is provided in the light source module 50, the light guide members 71c, which are provided in the light source module 50, are different members from the light guide members 71c which are provided on the connector 25b side.

As illustrated in FIG. 2B, when the light separator 81 is provided in the operation portion 23, the light guide member 71b, which is provided in the light source module 50, is a different member from the light guide member 71b which is provided on the connector 25b side.

Figure 2C:
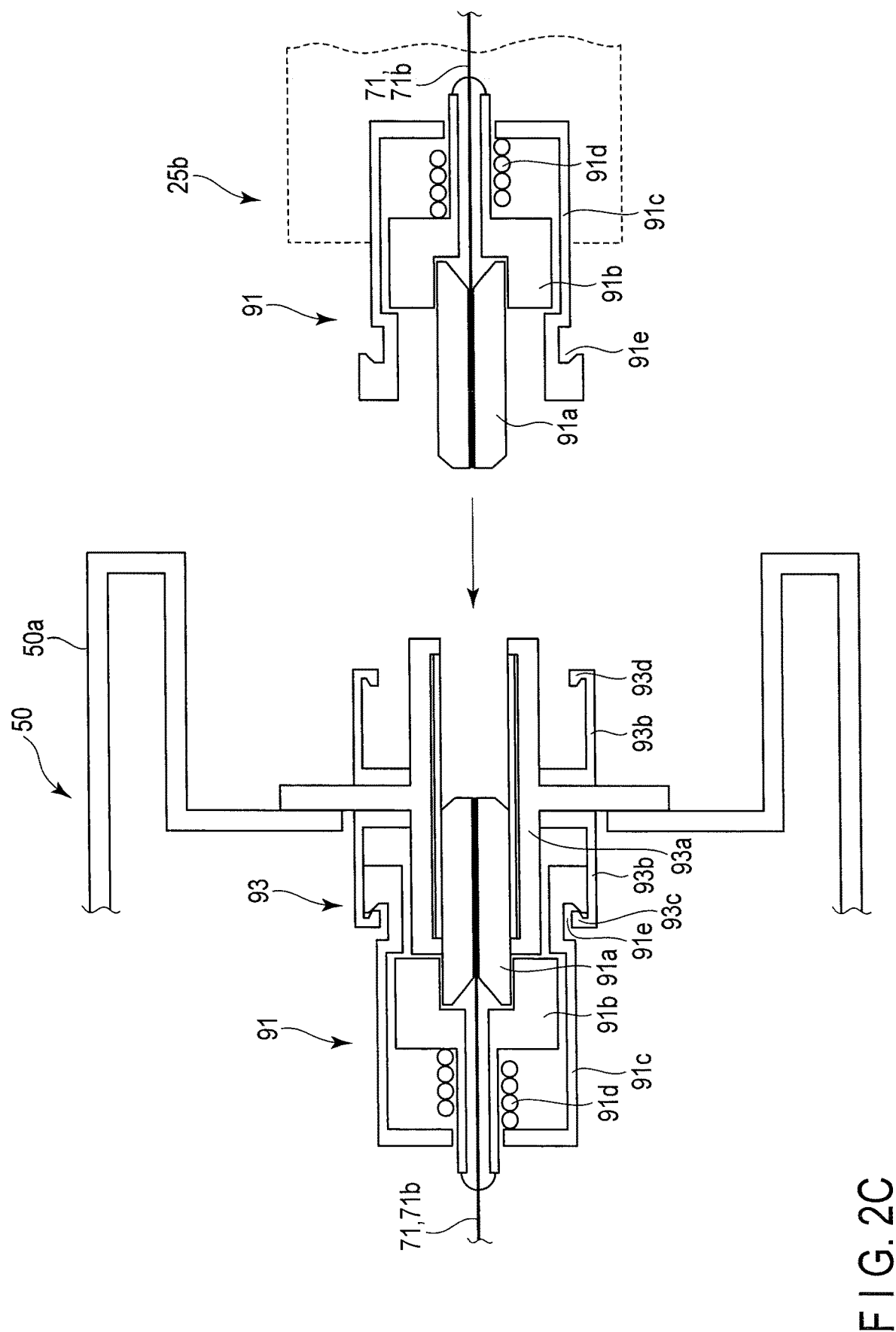
FIG. 2C is a view for describing a method of optically connecting a light guide member provided on a light source module side and a light guide member provided on a connector side.
Figure 2D:
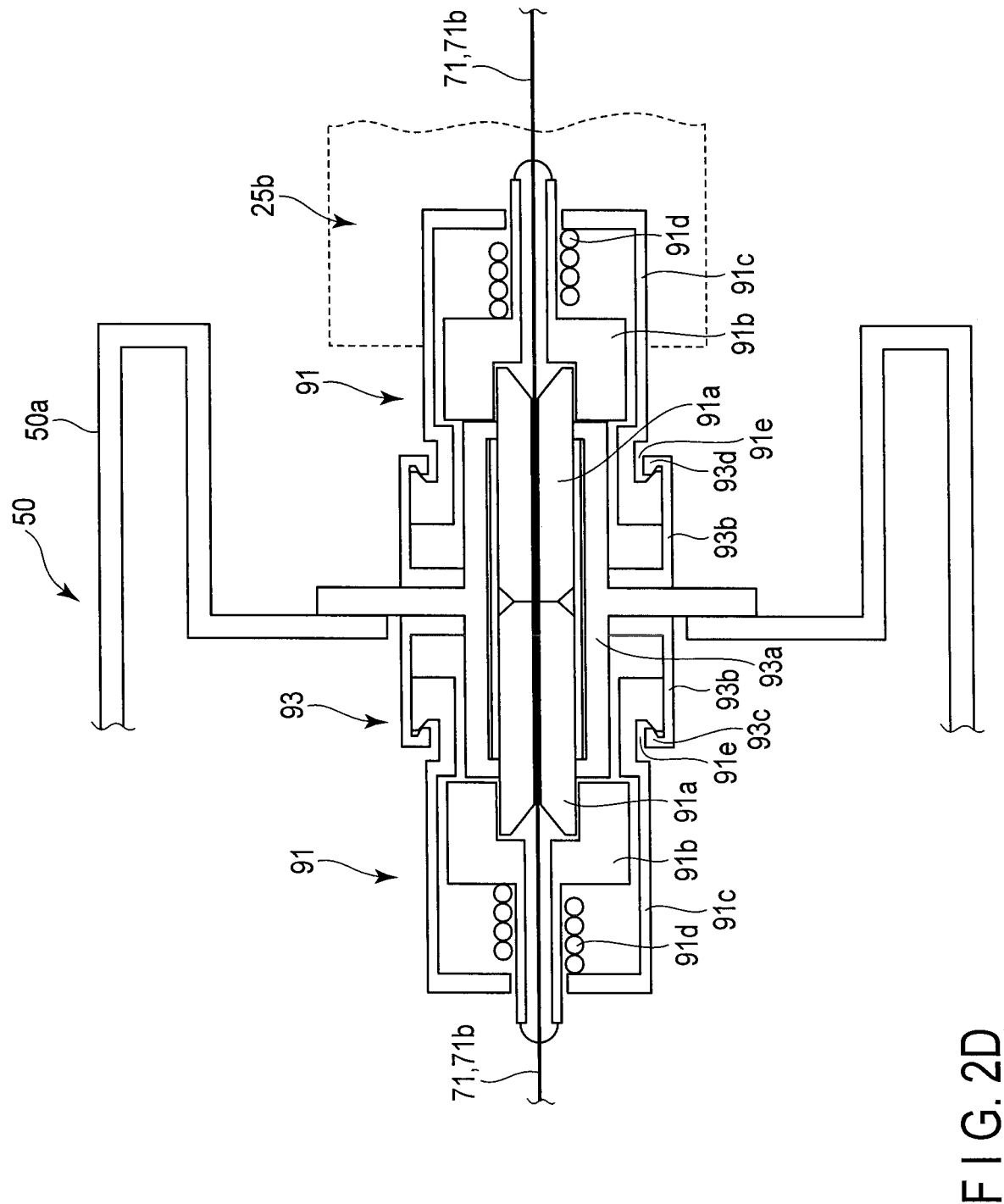
FIG. 2D is a view for describing the method of optically connecting the light guide member provided on the light source module side and the light guide member provided on the connector side.

Here, referring to FIG. 2C and FIG. 2D, a brief description is given of a method in which the light guide member 71b provided on the light source module 50 side illustrated in FIG. 2B is optically connected to the light guide member 71b provided on the connector 25b side.

As illustrated in FIG. 2C, as regards the light guide member 71b provided on the light source module 50, the light guide member 71b is provided in the light source module 50 and is inserted in a plug unit (plug) 91 which holds the light guide member 71b. Specifically, the plug unit 91 includes a ferrule 91a which holds the light guide member 71b, and a flange member (flange) 91b in which the ferrule 91a is detachably fitted. The plug unit 91 includes an exterior member (exterior) 91c with which the flange member 91b is engaged, and a pressing member 91d which is wound around the flange member 91b and presses the flange member 91b onto the exterior member 91c. The pressing member 91d presses, via the flange member 91b, the ferrule 91a and light guide member 71b toward a plug unit 91 that is provided on the connector 25b side. The pressing member 91d includes a coil spring which is expandable/contractible in an axial direction.

As illustrated in FIG. 2C, the above-described content also applies to the light guide member 71b provided on the connector 25b side. The plug unit 91 on the connector 25b side is provided in the connector 25b.

As illustrated in FIG. 2C, the housing 50a of the light source module 50 includes a light adapter 93 which is fixed to the housing 50a. The ferrule 91a on the light source module 50 side is inserted into a sleeve 93a of the light adapter 93 from one end portion of the sleeve 93a. The plug unit 91 on the light source module 50 side is attached in advance to the light adapter 93, so that the ferrule 91a is fixed to the sleeve 93a. The sleeve 93a is engaged with an exterior member 93b that is fixed to the housing 50a. The exterior member 93b of the light adapter 93 includes a first engaging portion 93c which is engaged in a groove (groove portion) 91e that is provided on an outer peripheral surface of the exterior member 91c on the light guide member 71b side.

As illustrated in FIG. 2D, if a plug unit 91 on the connector 25b side is inserted in the light adapter 93, a ferrule 91a on the connector 25b side is inserted in the light adapter 93 from the other end portion of the sleeve 93a of the light adapter 93. Then, a second engaging portion 93d, which is provided on the exterior member 93b of the light adapter 93, is engaged in a groove 91e that is provided on an outer peripheral surface of an exterior member 91c on the connector 25b side. Thereby, the light guide member 71b on the light source module 50 side is optically connected to the light guide member 71b on the connector 25b side. The second engaging portion 93d is a separate body from the first engaging portion 93c, and is provided on a side opposite to the first engaging portion 93c in the direction of insertion/removal of the plug unit 91 on the connector 25b side. The plug unit 91 on the connector 25b side is attachable/detachable to/from the light adapter 93 of the light source module 50.

The above-described content is substantially similarly applicable to the optical connection between the light guide members 71c illustrated in FIG. 2A.

As illustrated in FIG. 2A, the light connector 73 is provided, for example, in the inside of the housing 23a of the operation portion 23. In this manner, the light connector 73 is provided on an outside of the insertion module 21. The light connector 73 is provided between the light separator 81 and irradiation module 75 in the direction of travel of the light-source light, and is provided closer to the irradiation module 75 than to the light separator 81. In other words, the light connector 73 is provided on a forward side of the light separator 81 and on a backward side of the irradiation module 75 in the direction of travel of the light-source light.

The light connector 73 includes two input ports and one output port. For example, the light connector 73 is optically connected, at the input ports, to the light guide member 71c and the auxiliary light guide member 121b of the auxiliary light guide path 121, and is optically connected, at the output port, to the light guide member 71d. In addition, the light connector 73 optically connects an auxiliary optical fiber (to be described later) in the auxiliary light guide member 121b of the auxiliary light guide path 121 to at least one optical fiber in the light guide path 71. This optical fiber designates, for example, at least one of the two optical fibers in the light guide members 71c. Thus, the light connector 73 passes, individually, the light-source light which was guided by the light guide member 71c, and the auxiliary light which was guided from the guide mouth portion 130 (to be described later).

As illustrated in FIG. 2A, the irradiation module 75 is provided in the inside of a distal end portion of the insertion module 21. The irradiation module 75 includes a plurality of light converters (light conversion portions) 75a. One light converter 75a is optically connected to the light guide member 71c, and converts the light-source light, which is guided by the light guide member 71c, to illumination light. The other light converter 75a is optically connected to the light guide member 71d, and converts the light-source light or auxiliary light, which is guided by the light guide member 71d, to illumination light. The light converters 75a may convert the light-source light and auxiliary light to illumination light at the same time.

These light converters 75a may have a function of changing divergence angles of the light and auxiliary light, which are laser beams. In this case, the light converters 75a include, for example, diffusion members, convert the light-source light and auxiliary light to optimal illumination lights by the diffusion members, and radiate the illumination lights to the outside from the distal end portion of the insertion module 21.

As illustrated in FIG. 1, FIG. 2A and FIG. 2B, the light source system 70 further includes an auxiliary unit 100 which emits auxiliary light and guides the auxiliary light to the single optical fiber in the light guide path 71. The auxiliary unit 100 is a separate body from the endoscope 20, and is provided the outside of the endoscope 20.

As illustrated in FIG. 1, FIG. 2A and FIG. 2B, the auxiliary unit 100 includes an auxiliary light source module 110 which emits auxiliary light. The auxiliary light source module 110 includes a housing (housing portion) 110a having desired rigidity. The auxiliary light source module 110 is a separate body from the endoscope 20, and is provided the outside of the endoscope 20. The auxiliary light source module 110 is a separate body from the light source module 50.

As illustrated in FIG. 2A, the auxiliary light source module 110 includes an auxiliary light source 111 which emits auxiliary light, and is different from the light sources 51V, 51B, 51G and 51R. The auxiliary light source 111 is provided in the inside of the housing 110a. The auxiliary light source 111 is supplied with power, driven and controlled, independently from the light sources 51V, 51B, 51G and 51R.

It is preferable that the auxiliary light source 111 emits white light as the auxiliary light, or emits, as the auxiliary light, light-source light having a wavelength which is equal to at least one wavelength of the wavelengths of the light-source lights which are emitted from the light sources 51V, 51B, 51G and 51R.

The auxiliary light source module 110 may include a plurality of auxiliary light sources 111. In this case, the auxiliary light source module 110 may include a light coupler or a light separator.

The auxiliary light source module 110 is connected to, for example, the operation portion 23 of the endoscope 20 and outputs auxiliary light, when the light intensity of illumination light decreased or illumination was lost due to a fault of a part of the light source system 70, for example, a member having a sole optical function, such as the light coupler 57 or light separator 81. Thereby, even if illumination light by light-source light is not emitted, illumination light by auxiliary light can be emitted. As described above, the member having the sole optical function is a member which has only one predetermined optical function, and is a member which exhibits only one predetermined optical function, at a predetermined position in the light source system 70. In this case, for example, the light separator 81 is the only member having the light separate function at a predetermined position in the light source system 70.

As illustrated in FIG. 2A and FIG. 2B, the auxiliary unit 100 includes the auxiliary light guide path 121 which guides auxiliary light that was emitted from the auxiliary light source 111. The auxiliary light guide path 121 includes an auxiliary light guide member (auxiliary light guide) 121a which is optically connected to the auxiliary light source 111, and the auxiliary light guide member 121b which is optically connected to the light connector 73. Such a configuration may be adopted that the auxiliary light guide member 121a is omitted and the auxiliary light source 111 is directly optically connected to the auxiliary light guide member 121b in the guide mouth portion 130.

As illustrated in FIG. 2A and FIG. 2B, the auxiliary light guide member 121a is inserted through an auxiliary universal cord 123 including a housing (housing portion) 123a having flexibility and having desired rigidity. The auxiliary universal cord 123 is attachable/detachable to/from the auxiliary light source module 110. The auxiliary universal cord 123 includes an auxiliary connector (auxiliary connection portion) 123b which is attachable/detachable to/from the guide mouth portion 130. The auxiliary universal cord 123 is provided the outside of the endoscope 20, and is a separate body from the endoscope 20. The auxiliary light guide member 121b is provided in the inside of the housing 23a of the operation portion 23. The auxiliary light guide member 121a is provided the outside of the endoscope 20, and the auxiliary light guide member 121b is provided the inside of the endoscope 20. The auxiliary light guide member 121a is a separate body from the auxiliary light guide member 121b.

As illustrated in FIG. 2A and FIG. 2B, the auxiliary connector 123b is attached to the guide mouth portion 130, and thereby the auxiliary light guide member 121a is optically connected to the auxiliary light guide member 121b. The optical connection between the auxiliary light guide members 121a and 121b will be described later. In addition, the auxiliary light guide member 121a guides auxiliary light which was emitted from the auxiliary light source 111. The auxiliary light guide member 121b guides the auxiliary light, which was guided by the auxiliary light guide member 121a, to the light guide member 71d via the light connector 73.

The auxiliary light guide member 121a, 121b includes a single auxiliary optical fiber. The auxiliary optical fiber is a separate body from the single optical fibers in the light guide members 71a, 71b, 71c and 71d. The optical fiber in the auxiliary light guide member 121b guides the auxiliary light, which was guided from the guide mouth portion 130, to the optical fiber in the light guide member 71d.

In the meantime, in the present embodiment, although the single optical fiber is provided over the entirety of the auxiliary light guide path 121, the restriction to this is unnecessary. It should suffice if the single optical fiber is provided on at least a part of the auxiliary light guide path 121. If the single optical fiber is provided on a part of the auxiliary light guide path 121, a bundle fiber may be provided on the other part of the auxiliary light guide path 121.

As illustrated in FIG. 1, FIG. 2A and FIG. 2B, the light source system 70 further includes the guide mouth portion (light entrance) 130 which is detachably optically connected to the auxiliary light source module 110 that emits auxiliary light and is provided on the outside of the endoscope 20, and which is always optically connected to the auxiliary light guide member 121b of the auxiliary light guide path 121 that is provided in the inside of the endoscope 20. When the guide mouth portion 130 is connected to the auxiliary light source module 110, the guide mouth portion 130 guides the auxiliary light, which was emitted from the auxiliary light source module 110, to the auxiliary light guide path 121 that is provided in the inside of the endoscope 20.

As illustrated in FIG. 1, FIG. 2A and FIG. 2B, the guide mouth, portion 130 is provided in the endoscope 20. For example, the guide mouth portion 130 is provided in the housing 23a of the operation portion 23. In a state illustrated in FIG. 3A before the attachment of the auxiliary connector 123b to the guide mouth portion 130, the guide mouth portion 130 liquid-tightly seals the endoscope 20 including the insertion module 21 from an outer space portion. Thus, the guide mouth portion 130 includes a cap (cap portion) 131 which caps the guide mouth portion 130.

When the auxiliary unit 100 is used as illustrated in FIG. 1, the cap 131 is provided such that the light adapter 93, which is an auxiliary connector (auxiliary connection member (to be described later)), is exposed by the cap 131 being broken, as illustrated in FIG. 3B. If the cap 131 is broken, the plug unit 91 on the auxiliary connector 123b side can be inserted in the light adapter 93.

Figure 3A:
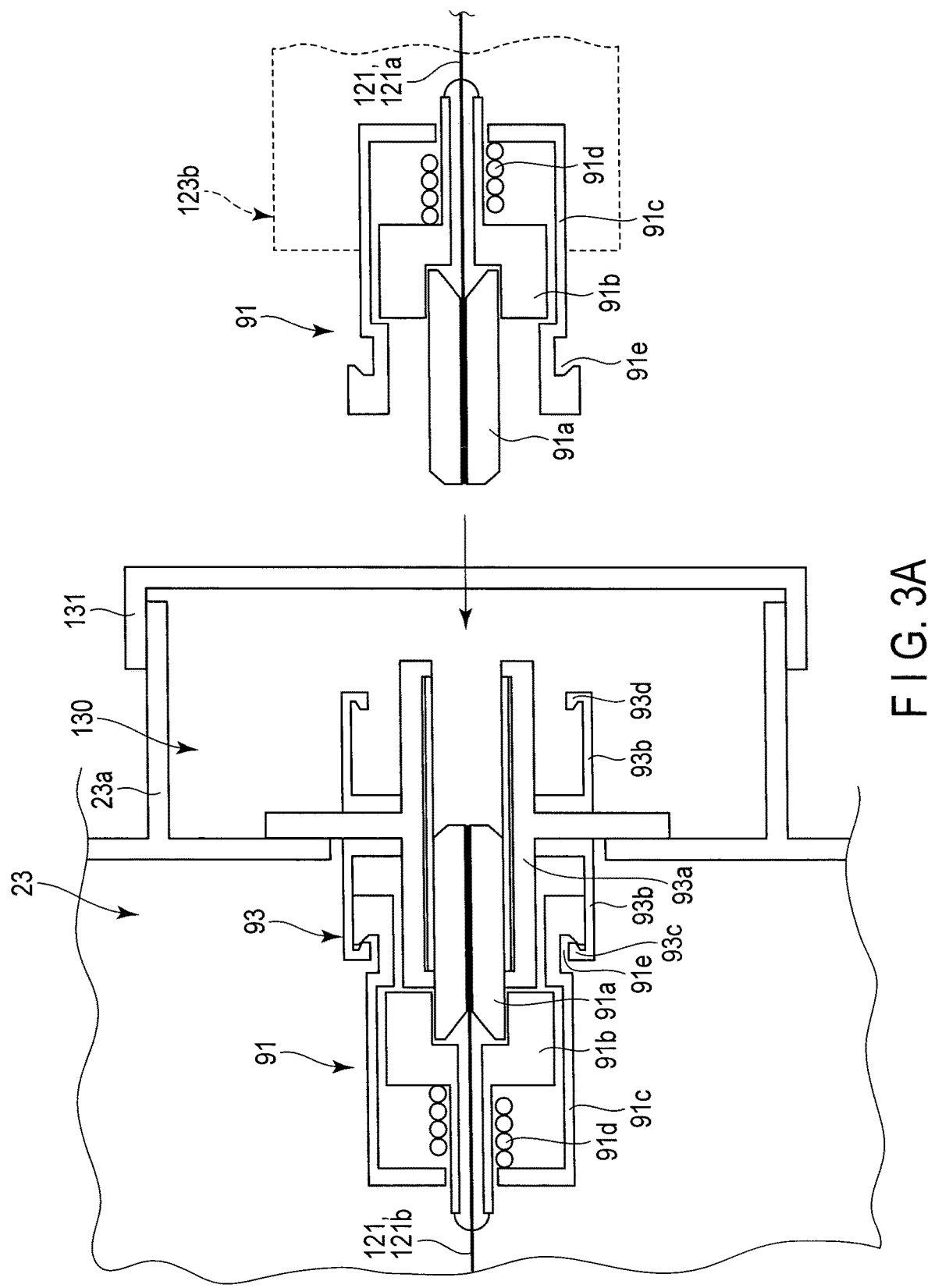
FIG. 3A is a view for describing a method of optically connecting a light guide member provided on an auxiliary connector side and a light guide member provided on a guide mouth portion side.

Here, referring to FIG. 3A and FIG. 3B, a brief description is given of a method in which the auxiliary light guide member 121b is optically connected to the auxiliary light guide member 121a. This connection is implemented in the guide mouth portion 130.

As illustrated in FIG. 3A, the auxiliary light guide member 121b is provided in the operation portion 23, and is inserted in the plug unit 91 which holds the auxiliary light guide member 121b. Specifically, the plug unit 91 includes a ferrule 91a which holds the auxiliary light guide member 121b, and a flange member (flange) 91b in which the ferrule 91a is detachably fitted. The plug unit 91 includes an exterior member (exterior) 91c with which the flange member 91b is engaged, and a pressing member 91d which is wound around the flange member 91b and presses the flange member 91b onto the exterior member 91c. The pressing member 91d presses, via the flange member 91b, the ferrule 91a and auxiliary light guide member 121b toward a plug unit 91 that is provided on the auxiliary connector 123b side. The pressing member 91d includes a coil spring which is expandable/contractible in an axial direction.

As illustrated in FIG. 3A, the above-described content also applies to the auxiliary light guide member 121a provided on the auxiliary connector 123b side. The plug unit 91 on the auxiliary connector 123b side is provided in the auxiliary connector 123b.

As illustrated in FIG. 3A, the guide mouth portion 130 includes a light adapter 93 functioning as an auxiliary connector which is connected to the auxiliary connector 123b of the auxiliary light source module 110. The light adapter 93 is fixed to the guide mouth portion 130 in the housing 23a of the operation portion 23. In the light adapter 93, the ferrule 91a on the auxiliary light guide member 121b side is inserted into a sleeve 93a of the light adapter 93 from one end portion of the sleeve 93a. The plug unit 91 on the auxiliary light guide member 121b side is attached in advance to the light adapter 93, so that the ferrule 91a is fixed to the sleeve 93a. The sleeve 93a is engaged with an exterior member 93b that is fixed to the housing 23a. A first engaging portion 93c, which is provided on the exterior member 93b of the light adapter 93, is engaged in a groove 91e that is provided on an outer peripheral surface of the exterior member 91c on the auxiliary light guide member 121b side.

As illustrated in FIG. 3B, if the cap 131 is broken and the auxiliary connector 123b is inserted in the guide mouth portion 130, a ferrule 91a on the auxiliary light guide member 121a is inserted in the light adapter 93 from the other end portion of the sleeve 93a of the light adapter 93. Then, a second engaging portion 93d, which is provided on the exterior member 93b of the light adapter 93, is engaged in a groove 91e that is provided on an outer peripheral surface of an exterior member 91c on the auxiliary light guide member 121a side. Thereby, the auxiliary light guide member 121a is optically connected to the auxiliary light guide member 121b. The plug unit 91 on the auxiliary connector 123b side is attachable/detachable to/from the light adapter 93 of the guide mouth portion 130.

Figure 2E:
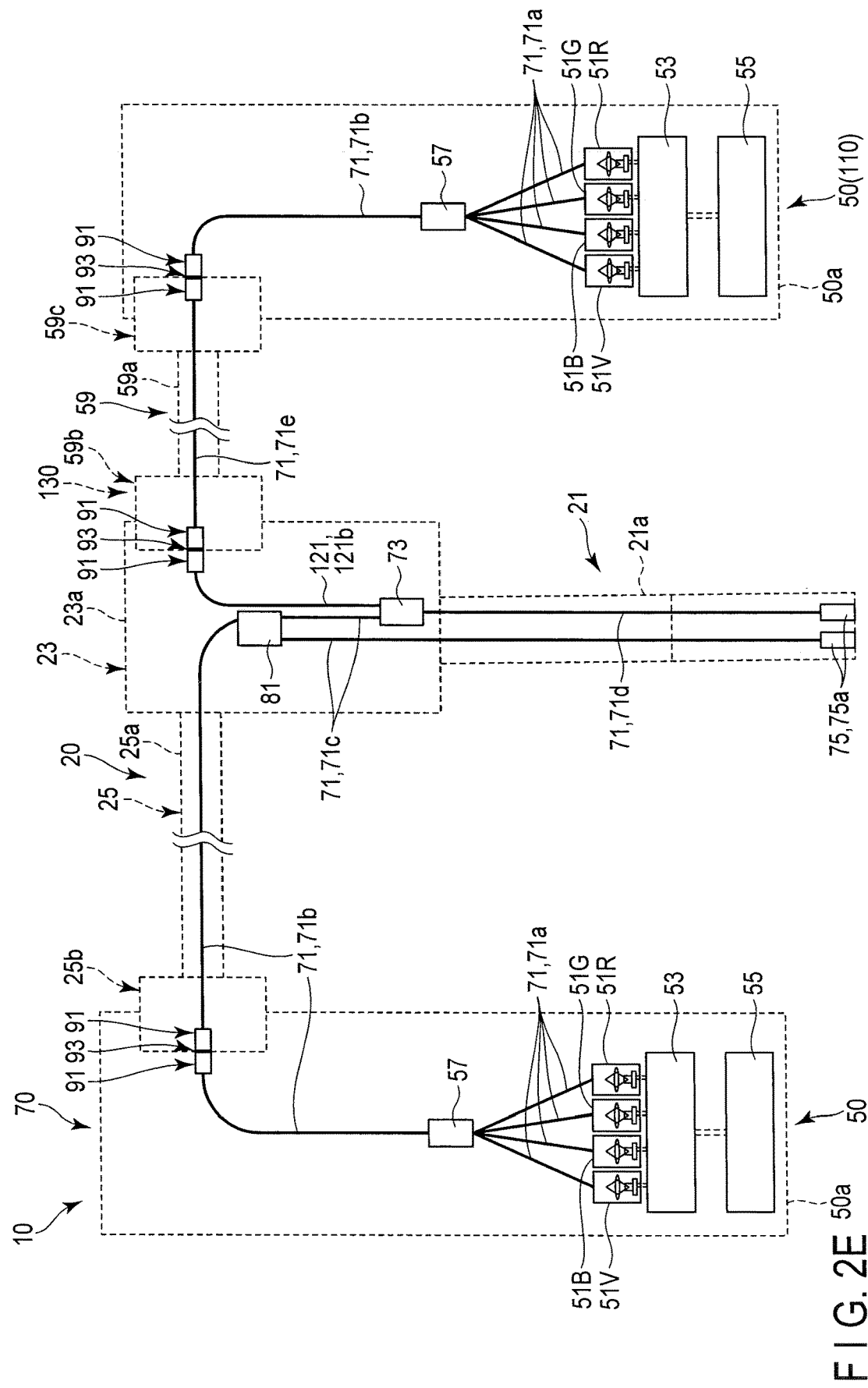
FIG. 2E is a schematic view of the endoscope light source system in a case in which the light source module functions as an auxiliary light source module.

In the meantime, although the auxiliary light source module 110 is the separate body from the light source module 50, another light source module 50 may be used as the auxiliary light source module 110 as illustrated in FIG. 2E.

When another light source module 50 is thus made to function as the auxiliary light source module 110, a universal cord 59 is further used. The universal cord 59 includes a light guide path 71 which is optically connectable to the light source module 50 and guide mouth portion 130 and guides light-source light, which was emitted from light sources, to the guide mouth portion 130. The light guide path 71 includes a light guide member (light guide) 71e.

The light guide member 71e includes, for example, a single optical fiber. The optical fiber is a separate body from the single optical fibers in the light guide members 71a, 71b, 71c, and 71d.

Although the single optical fiber is provided over the entirety of the light guide member 71e, the restriction to this is unnecessary. It should suffice if the single optical fiber is provided on at least a part of the light guide member 71e. If the single optical fiber is provided on a part of the light guide member 71e, a bundle fiber may be provided on the other part of the light guide member 71e.

As illustrated in FIG. 2E, the universal cord 59 includes a housing (housing portion) 59a which has flexibility and has desired rigidity. The universal cord 59 includes a connector 59b which is provided on one end portion of the universal cord 59 and is attachable/detachable to/from the guide mouth portion 130, and a connector (connection portion) 59c which is provided on the other end portion of the universal cord 59 and is attachable/detachable to/from the light source module 50. By the connector 59b being attached to the guide mouth portion 130, the light guide member 71e is optically connected to the auxiliary light guide member 121b. By the connector 59c being attached to the light source module 50, the light guide member 71e is optically connected to the light guide member 71b. The optical connection between the light guide member 71e and auxiliary light guide member 121b and the optical connection between the light guide members 71e and 71b are substantially the same as described above. The light guide member 71e guides light-source light which was emitted from the light sources. The auxiliary light guide member 121b guides the light, which was guided by the light guide member 71e, to the light guide member 71d as auxiliary light via the light connector 73.

In the above, two light source modules 50 are prepared, one of the light source modules 50 functions as a normal light source module, and the other light source module 50 functions as an auxiliary light source module 110. However, the restriction to this is unnecessary. For example, if it is determined that a fault occurred in the light guide member 71c in the universal cord 25, the light source module 50, which functions as the normal light source module, can be used as the auxiliary light source module 110 as such, although not illustrated.

In order to suppress a decrease in light intensity of illumination light, it is necessary to assume that a fault occurred in the respective members.

For example, even if one of the light sources 51V, 51B, 51G and 51R becomes faulty, the other three light sources are driven. Thus, a decrease in light intensity of illumination light can be suppressed.

In this manner, when a plurality of members having the same optical function are provided, and these members function independently, a decrease in light intensity of illumination light can be suppressed even if one of the members becomes faulty.

The above-described content also applies to the light guide member 71 and light converters 75*a*.

Unlike the above, the light coupler 57, light separator 81, light connector 73 and guide mouth portion 130 are provided as members having sole optical functions. The light connector 73 is a member which is disposed closest to the irradiation module 75, among the members having the sole optical functions. As described above, the member having the sole optical function is a member which has only one predetermined optical function, and is a member which exhibits only one predetermined optical function, at a predetermined position in the light source system 70.

Even if the light connector 73 becomes faulty, at least one light guide member 71*c* is optically connected to the irradiation module 75, as illustrated in FIG. 2A. Thus, a decrease in light intensity of illumination light can be prevented.

Even if the guide mouth portion 130 becomes faulty, since it is not used usually, there occurs no problem. In addition, the guide mouth portion 130 is provided in the housing 23*a* with rigidity, and is capped by the cap 131. Thus, it can be said that the probability of a fault of the guide mouth portion 130 is substantially zero.

On the other hand, if the light coupler 57 or light separator 81 becomes faulty, the light intensity of illumination light certainly decreases. In this case, in the present embodiment, auxiliary light is guided from the auxiliary light guide path 121 to the light guide path 71, and illumination light by the auxiliary light is emitted. Specifically, the auxiliary connector 123*b* is attached to the guide mouth portion 130, such that the auxiliary light guide member 121*a* is optically connected to the auxiliary light guide member 121*b*. The auxiliary light is emitted from the auxiliary light source 111. In addition, the auxiliary light is guided to the light connector 73 by the auxiliary light guide members 121*a* and 121*b*, is made incident on the light guide member 71*d* by the light connector 73, and is guided to the irradiation module 75 by the light guide member 71*d*. The auxiliary light is emitted to the outside as illumination light by the irradiation module 75. In this manner, since the light connector 73 is provided, the auxiliary light guide path 121 is optically connected to the light guide path 71 by the light connector 73. Thereby, the auxiliary light is guided from the auxiliary light guide path 121 to the light guide path 71, and further guided to the irradiation module 75. In addition, even when the light coupler 57 or light separator 81 became faulty and the light intensity decreased, the light intensity, which is in the decreased state, is increased by the auxiliary light which is guided from the auxiliary guide light path 121 which is optically connected to the light guide path 71 by the light connector 73.

The auxiliary connector 123*b* is attached to the guide mouth portion 130 at a timing when a fault occurred as described above.

As described above, in the present embodiment, even if the respective members become faulty individually, a decrease in light intensity of illumination light can be suppressed. In addition, even when the light coupler 57 or light separator 81, which is the member having the sole optical function, became faulty and the light intensity decreased, the light intensity, which is in the decreased state, is increased by the auxiliary light which is guided from the auxiliary guide light path 121 which is optically connected to the light guide path 71 by the light connector 73. Furthermore, in accordance with the above, the risk of loss of illumination light is decreased.

In the meantime, the light connector 73 is provided on the forward side of the light coupler 57 and light separator 81 in the direction of travel of light-source light, and is provided in proximity to the irradiation module 75. Thus, even when the light coupler 57 or light separator 81 became faulty and the light intensity decreased, the auxiliary light is surely supplied to the irradiation module 75. In addition, in the state in which the light intensity decreased, the light intensity is increased by the auxiliary light which is guided from the auxiliary guide light path 121 which is optically connected to the light guide path 71 by the light connector 73.

In the present embodiment, since the light connector 73 is provided, the auxiliary light guide path 121 can be optically connected to the light guide path 71, and the auxiliary light is guided from the auxiliary light guide path 121 to the light guide path 71. Thus, even when the member having the sole optical function became faulty and the light intensity decreased, the light intensity, which is in the decreased state, can be increased by the auxiliary light which is guided from the auxiliary guide light path 121 which is optically connected to the light guide path 71 by the light connector 73. In addition, even if the respective members become faulty individually, a decrease in light intensity of illumination light can be suppressed.

The light connector 73 is provided on the forward side of the light coupler 57 and light separator 81 in the direction of travel of light-source light, and is provided in proximity to the irradiation module 75. The light connector 73 is the member which is disposed closest to the irradiation module 75, among the members having the sole optical functions. Thus, even when the light coupler 57 or light separator 81, which is the member having the sole optical function, became faulty and the light intensity decreased, the auxiliary light, which is guided from the auxiliary guide light path 121 that is optically connected to the light guide path 71 by the light connector 73, can surely be supplied to the irradiation module 75. In addition, in the state in which the light intensity decreased, the light intensity can be increased by the auxiliary light which is guided from the auxiliary guide light path 121 which is optically connected to the light guide path 71 by the light connector 73.

The light connector 73 is provided on the outside of the insertion module 21. Thus, the light connector 73 is not affected by the bending of the insertion module 21, and the light connector 73 can be prevented from being broken by the bending.

The light connector 73 is provided in the inside of the housing 23*a* with rigidity. Thus, the light connector 73 can be prevented from being broken.

When the light guide members 71*a*, 71*b* and 71*c* are formed of only bundle fibers, even if some optical fibers of the bundle fibers become faulty, no decrease occurs in the light intensity of illumination light. However, when the light guide members 71*a*, 71*b* and 71*c* are formed of only single optical fibers, if these optical fibers become faulty, the light intensity of illumination light would certainly decrease. Even in such a situation, in the present embodiment, the light connector 73 optically connects the optical fiber in the auxiliary light guide member 121*b* to the optical fiber in the light guide member 71*d*. Thus, in the state in which the light intensity decreased, the light intensity can be increased by the auxiliary light.

In the light connector 73, the light guide member 71*d* is not a bundle fiber which is formed by bundling the single optical fiber of the light guide member 71*c* and the single optical fiber of the auxiliary light guide member 121*b*. The light guide member 71*d* is a single optical fiber, is a sole optical member which is shared by the light-source light and auxiliary light, and is a member having the sole optical function of guiding the light-source light and auxiliary light. Thus, between the light connector 73 and irradiation module 75, the light guide member 71*d* does not need to be provided individually for the light-source light and auxiliary light. Specifically, it is not necessary that the light guide member 71*d* for only the light-source light be provided, and the light guide member 71*d* for only the auxiliary light be provided. Since it suffices that only at least one light guide member 71*d* is provided between the light connector 73 and irradiation module 75, the thickness of the insertion module 21 can be reduced.

The optical fiber of the auxiliary light guide member 121*b* is optically connected to the optical fiber of the single light guide member 71*d* by the light connector 73. Thereby, in the state in which the light intensity decreased, the light intensity can be increased by the auxiliary light at low cost, with a saved space, and with a low weight.

When the light guide member 71*d* includes a plurality of optical fibers, the optical fiber of the auxiliary light guide member 121*b* is optically connected to the plural optical fibers of the light guide member 71*d* by the light connector 73. In this case, even if some of the optical fibers of the light guide member 71*d* are broken, the other optical fibers remain, and a decrease in light intensity of illumination light can further be suppressed.

By the above, the risk of loss of illumination light can be reduced.

The endoscope 20 can be liquid-tightly sealed by the cap 131, until the auxiliary connector 123*b* is connected to the guide mouth portion 130.

A situation in which auxiliary light is used is a situation in which a part of the light source system 70 became faulty. Thus, by the light adapter 93, which is the auxiliary connector, being exposed by the breakage of the cap 131, it is possible to prevent the faulty light source system 70 from being re-used.

The light source module 50 can be connected to the guide mouth portion 130 via the universal cord 59, and the light-source light travels from the light source module 50 to the guide mouth portion 130 (auxiliary light guide member) via the light guide path 71 that is provided in the universal cord 59. Thus, for example, when the light guide member 71*c* shown in FIG. 2E or the light guide member 71*b* on the endoscope 20 side became faulty and the light source module 50 is normal, the light source module 50 can be utilized, and a work for preparing the auxiliary light source module 110 can be omitted.

The auxiliary light source 111 is different from the light sources 51V, 51B, 51G and 51R, and is a separate light source from the light sources 51V, 51B, 51G and 51R. Thus, even if the light sources 51V, 51B, 51G and 51R become faulty, the auxiliary light source 111 can emit auxiliary light, without being affected by the fault.

The auxiliary light source 111 is supplied with power, driven and controlled, independently from the light sources 51V, 51B, 51G and 51R. Thus, the auxiliary light source 111 can emit auxiliary light, without being affected by the states of the light sources 51V, 51B, 51G and 51R.

In the meantime, the auxiliary light source module 110 may include an auxiliary controller (auxiliary control portion) which controls, based on a detection result of a detector (detection portion (not shown)), the emission of auxiliary light of the auxiliary light source 111. The detector is provided in the auxiliary connector 123*b*. When the auxiliary connector 123*b* was attached to the guide mouth portion 130, the detector detects light which travels from the light converter 75*a* to the detector. When the detector has detected light of a predetermined value or more, the auxiliary controller controls the auxiliary light source 111 so that the auxiliary light source 111 emits auxiliary light having a preset light intensity. The detector includes a photodiode or the like, which receives the light that traveled from the light converter 75*a* to the detector.

The auxiliary light source 111 emits white light. Thereby, the auxiliary light source 111 can function as a substitute for the light sources 51V, 51B, 51G and 51R.

The auxiliary light source 111 emits, for example, auxiliary light having the same wavelength as the wavelength of light-source light which the light source 51V emits. Thereby, the auxiliary light source ill can function as a substitute for the light source 51V.

Incidentally, the light sources 51V, 51B, 51G and 51R may include LEDs or lamps. Although the light sources 51V, 51B, 51G and 51R are provided, the number of light sources is not particularly limited.

The light coupler 57 may be a spatial optical system using a lens, a half-mirror and a dielectric mirror. This point similarly applies to the light separator 81.

Second Embodiment

Hereinafter, referring to FIG. 4A, FIG. 4B, FIG. 4C and FIG. 4D, a description will be given of only the points different from the first embodiment.

In the endoscope system 10 of the first embodiment, the endoscope 20 is directly connected to various devices via the universal cord 25 including the connector 25*b*.

However, in the present embodiment, as illustrated in FIG. 4A, the universal cord 25 is omitted, and the endoscope 20 is configured as a wireless type. In this case, the endoscope 20 is of such a wireless type that radio signals are transmitted/received between the operation portion 23 and image processor 30.

The light source system 70 of the present embodiment uses light of a narrow band. Thus, as illustrated in FIG. 4B, for example, light sources 51V and 51B are provided. Light-source light emitted from the light source 51V, 51B has such a wavelength as to excite a phosphor mounted on the irradiation module 75.

As illustrated in FIG. 4B, the light source system 70 includes a radio portion 201 which is provided in the image processor 30 and outputs radio signals for controlling, for example, the light sources 51V and 51B and the imager; and a controller (control portion) 203 which is electrically connected to the radio portion 201 and controls the endoscope system 10. The radio portion 201 and controller 203 are provided in the inside of the housing 30a having desired rigidity. The controller 203 have, for example, a hardware circuitry including ASIC.

As illustrated in FIG. 4B, in the present embodiment, the light sources 51V and 51B are provided in the inside of the housing 23a of the operation portion 23.

As illustrated in FIG. 4B, the light source system 70 further includes a radio portion 211 which receives a radio signal that was output from the radio portion 201; and a controller (control portion) 213 which controls the light sources 51V and 51B, based on the radio signal received by the radio portion 211. The radio portion 211 and controller 213 are provided in the inside of the housing 23a of the operation portion 23. The light sources 51y and 51B are mounted on a control board (not shown) on which the controller 213 is formed. The controller 213 have, for example, a hardware circuitry including ASIC.

As illustrated in FIG. 4B, the light source system 70 further includes a supply portion 215 which supplies energy to the radio portion 211, controller 213 and light sources 51V and 51B. The supply portion 215 is provided in the inside of the housing 23a of the operation portion 23. The supply portion 215 includes, for example, a battery which supplies energy that is electric power. The supply portion 215 also supplies energy to the respective members of the endoscope 20.

The above-described radio portion 201, controller 203, radio portion 211 and controller 213 function as a radio unit of the light source system 70 which is mounted in the wireless-type endoscope system 10.

The radio portion 201 may transmit a signal, which includes a driving condition of the light sources 51V and 51B, to the radio portion 211. Based on this driving condition, the controller 213 controls the light sources 51V and 51B.

The radio portion 211 may generate a video signal based on an imaging signal of a to-be-illuminated object which was imaged by the imager (not shown), may convert the video signal to a radio signal, and may transmit the radio signal to the radio portion 201. The controller 203 converts the radio signal to a video signal, and executes image processing on the video signal. The display 40 displays the video signal as a video image.

The radio portion 211 may transmit residual amount information, which indicates a residual amount of energy in the supply portion 215, to the radio portion 201. In addition, the display 40 may display this residual amount information.

In this manner, various pieces of information are transmitted/received between the radio portions 201 and 211.

As illustrated in FIG. 4B, the light sources 51V and 51B are provided in the inside of the housing 23a of the operation portion 23. Thus, in consideration of the space in the housing 23a, the light source system 70 includes a light coupling/separating portion 217 which is provided in the inside of the housing 23a of the operation portion 23 and has the function of the light coupler 57 and the function of the light separator 81 in the first embodiment. The light coupling/separating portion 217 functions as a light combiner and a light separator.

As illustrated in FIG. 4B, the light coupling/separating portion 217 is optically connected to a light guide member 71a which is optically connected to the light source 51V, and also optically connected to a light guide member 71a which is optically connected to the light source 51B. The light coupling/separating portion 217 is further optically connected to a light guide member 71c which is optically connected to the irradiation module 75, and also optically connected to a light guide member 71c which is optically connected to the light connector 73. In this manner, the light coupling/separating portion 217 includes two input ports and two output ports. The number of input ports of the light coupling/separating portion 217 is equal to the number of light sources. The number of output ports is not particularly limited, if the number is plural. In other words, it should suffice if the number of light guide members 71c is plural.

The light coupling/separating portion 217 couples into single light the light-source light which was emitted from the light source 51V and guided by the light guide member 71a, and the light-source light which was emitted from the light source 51B and guided by the light guide member 71a.

The light coupling/separating portion 217 separates the coupled single light-source light into a plurality of lights. The light coupling/separating portion 217 separates the light-source light, for example, at a desired ratio. In this embodiment, the ratio is, for example, 50:50. It is not necessary that the ratio be equal between the respective output ports.

The light converters 75a include wavelength conversion members which wavelength-convert the light-source light and auxiliary light to illumination light. The wavelength conversion member includes, for example, a phosphor. The wavelength conversion member may be a unit in which a plurality of wavelength conversion members are combined. When the wavelength conversion member converts the light-source light and auxiliary light to illumination light, the wavelength conversion member may include a member which converts the optical characteristics of the light-source light and the optical characteristics of the auxiliary light. Such a member includes, for example, a diffusion member which widens the light distribution of light-source light and the light distribution of auxiliary light, and a reflector which efficiently emits illumination light from the distal end portion.

Figure 4C:
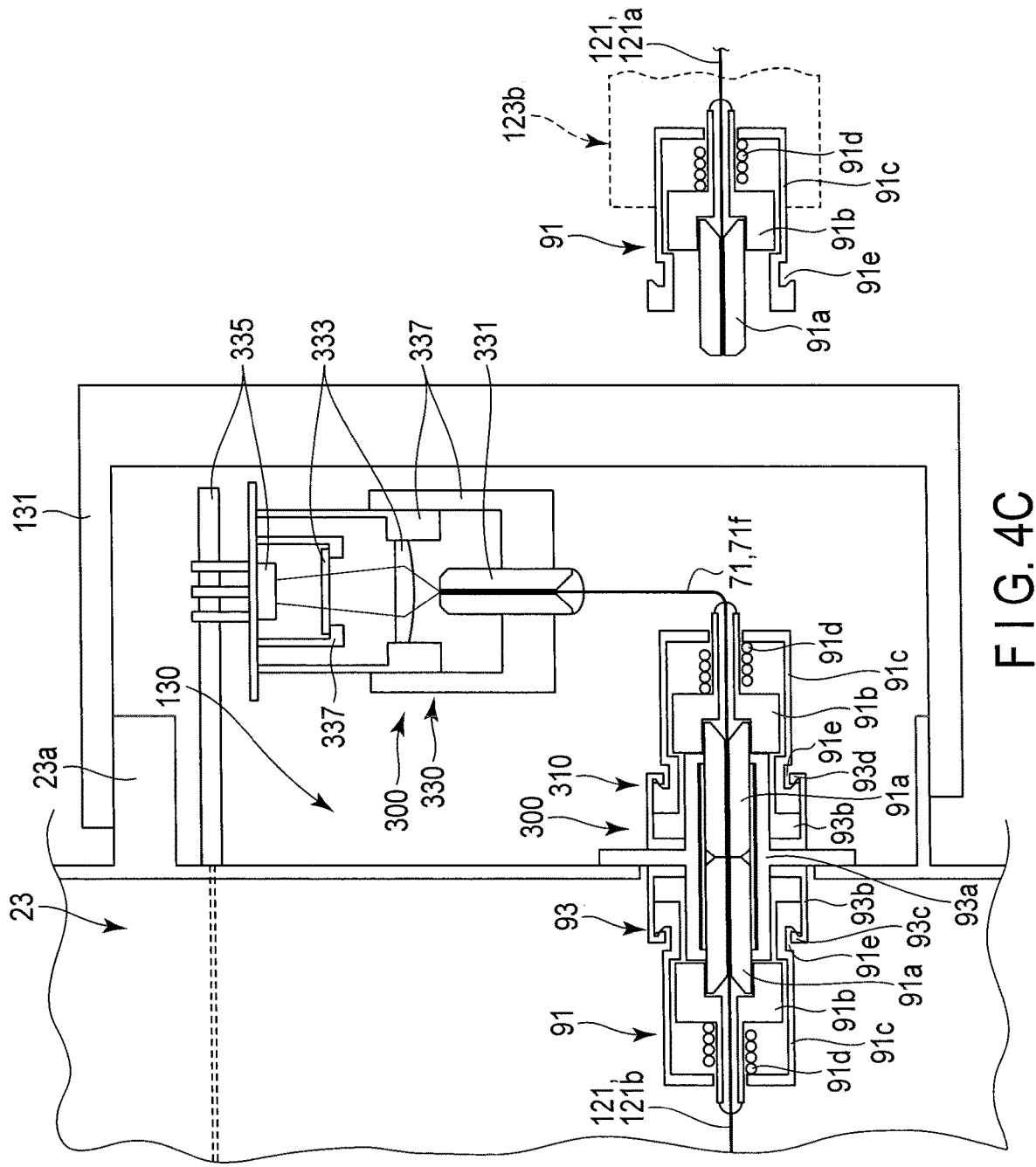
FIG. 4C is a view for describing a state in which a detection unit is connected to a light adapter provided on the guide mouth portion side, and the detection unit is detecting return light.
Figure 4D:
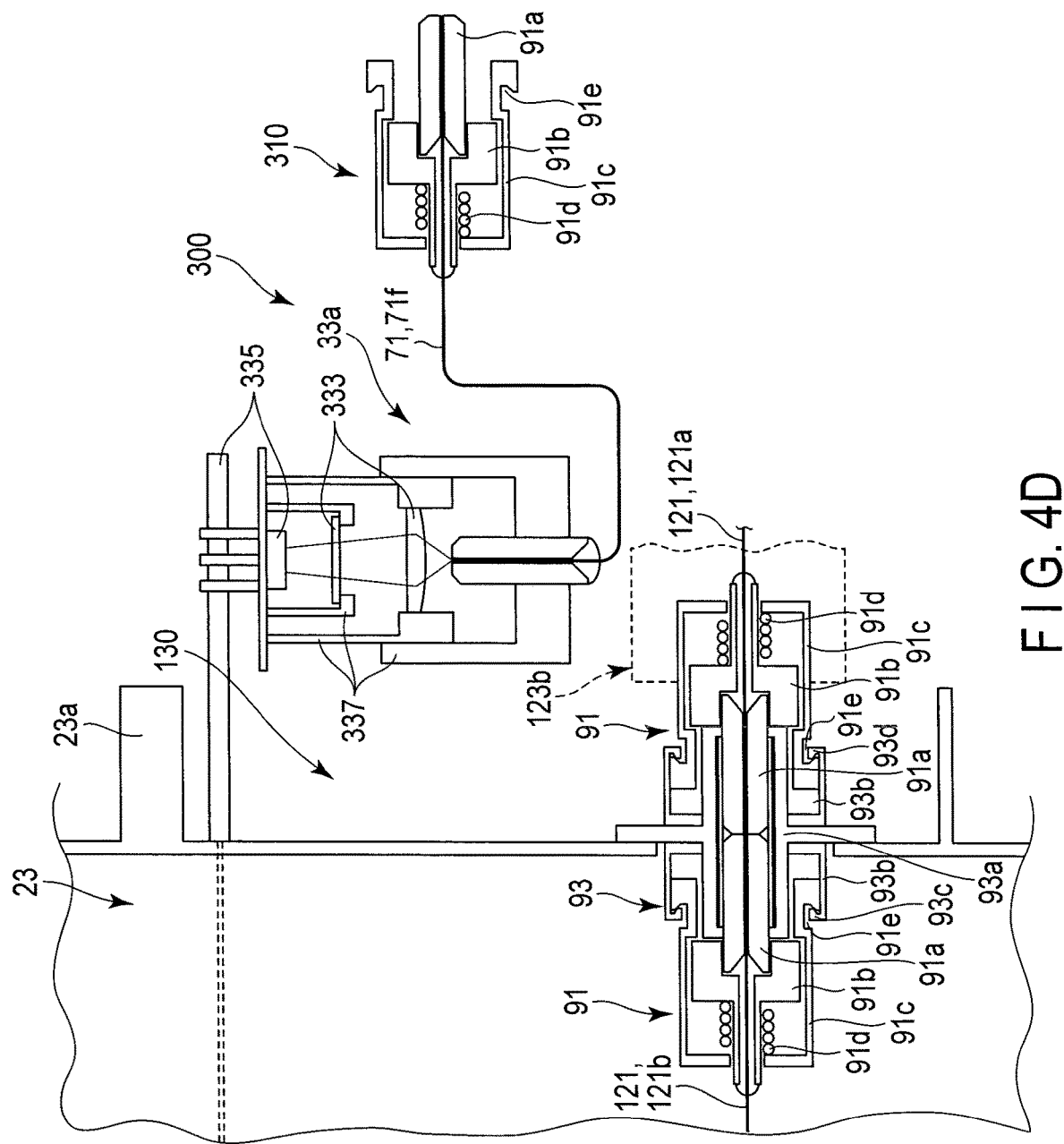
FIG. 4D is a view for describing a method of optically connecting a light guide member provided on an auxiliary connector side and a light guide member provided on the guide mouth portion side, while the detection unit is disconnected from the light adapter provided on the guide mouth portion side.

As illustrated in FIG. 4B, FIG. 4C and FIG. 4D, the light source system 70 further includes a detection unit (detector) 300 which is provided in the guide mouth portion 130 in the housing 23a of the operation portion 23.

As illustrated in FIG. 4C, the detection unit 300 is covered with the cap 131. As illustrated in FIG. 4C and FIG. 4D, the detection unit 300 is attachable/detachable to/from the light adapter 93 which functions as an auxiliary connector (auxiliary connection member) such that the detection unit 300 is optically connectable to the auxiliary light guide path 121 provided in the endoscope 20. The detection unit 300 detects the light intensity of light which travels from the irradiation module 75 to the detection unit 300. As illustrated in FIG. 4C, when only the light source module 50 (light sources 51V and 51B) is used, the detection unit 300 is attached to the light adapter 93. As illustrated in FIG. 4D, when only the auxiliary light source module 110 is used, the detection unit 300 is detached from the light adapter 93.

As illustrated in FIG. 4C and FIG. 4D, the detection unit 300 includes a detection connector (detection connection portion) 310 which is attachable/detachable to/from the light adapter 93, and a detector (detection portion) 330. The detection connector 310 is connected to the detector 330, for example, by a light guide member 71f. The light guide member 71f includes a single optical fiber. One end portion of the light guide member 71f is held by the detection connector 310, and the other end portion of the light guide member 71f is held by the detector 330. Thus, the detection connector 310 is mechanically and optically connected to the detector 330.

As illustrated in FIG. 4C, since the detection connector 310 has the same structure as the plug unit 91 on the auxiliary connector 123b side, a detailed description thereof is omitted. The ferrule 91a on the detection connector 310 side is inserted into the light adapter 93 from the other end portion of the sleeve 93a of the light adapter 93. Then, the second engaging portion 93d, which is provided on the exterior member 93b of the light adapter 93, is engaged in the groove 91e that is provided on the outer peripheral surface of the exterior member 91c on the detection connector 310 side. Thereby, the light guide member 71f is optically connected to the auxiliary light guide member 121b.

As illustrated in FIG. 4C, the detector 330 is fixed to the housing 23a of the operation portion 23 which is provided with the guide mouth portion 130. The detector 330 detects light which is guided by the light guide member 71f. This light is light which travels from the light converter 75a to the detector 330. Normally, when the light-source light, which was emitted from the light source 51V, 51B, is converted to illumination light by the light converter 75a, the light-source light is diffused or scattered by the phosphor or the like. At this time, part of the illumination light is not emitted from the light converter 75a, and this part becomes return light which reversely travels through the light guide member 71d and travels through the auxiliary light guide member 121b. Incidentally, the return light includes a laser beam which is not converted to the illumination light by the light converter 75a, and reversely travels through the light guide member 71d and travels through the auxiliary light guide member 121b. In addition, the return light includes a laser beam which does not travel to the light converter 75a from the light connector 73, and travels from the light connector 73 to the auxiliary light guide member 121b by the light connector 73. For this return light, the light connector 73 functions as a light separator, and separates part of the return light to the auxiliary light guide member 121b. In addition, the separated part of return light is guided by the auxiliary light guide member 121b, and guided to the light guide member 71f via the detection connector 31. The detector 330 detects this light.

As illustrated in FIG. 4C, the detector 330 includes a ferrule 331 which holds the other end portion of the light guide member 71f, and a light focusing unit 333 (for example, lens) which focuses the return light that was guided by the light guide member 71f and emitted from the light guide member 71f. The detector 330 further includes a detection main portion 335 which receives the light focused by the light focusing unit 333, and detects the light intensity of the received return light. The detection main portion 335 is fixed to the housing 23a. The detector 330 further includes a holder (holding unit) 337 which holds the ferrule 331, light focusing unit 333 and detection main portion 335.

As illustrated in FIG. 4B and FIG. 4C, the detection main portion 335 is electrically connected to the controller 213, and transmits a detection result to the controller 213. The detection result is transmitted to the controller 203 via the radio portions 211 and 201. The detection result may be transmitted, for example, constantly while the endoscope system 10 is being driven, or may be transmitted while the light sources 51V and 51B are being driven.

As illustrated in FIG. 4B, the controller 203 includes a judgment portion 205 which judges whether the detection result is a normal value or is other than the normal value. When the judgment portion 205 judged that the detection result is other than the normal value, the controller 203 controls the display 40 so that the display 40 displays to that effect. Thus, the display 40 displays that the detection result is other than the normal value, or in other words, that abnormality occurs, and an alert is issued to the operator. In this manner, monitoring is performed for the respective members. After the alert was issued, the detection unit 300 is detached from the light adapter 93, and the auxiliary light source module 110 is connected to the light adapter 93.

As illustrated in FIG. 4D, the cap 131 is broken and the detection connector 310 of the detection unit 300 is detached from the light adapter 93. In this state, the auxiliary light guide member 121a is optically connected to the auxiliary light guide member 121b, and the light adapter 93 is connected to the auxiliary light source module 110 side (auxiliary connector 123b) such that auxiliary light is guided to the light guide path 71 via the auxiliary light guide path 121.

In the above, the judgment portion 205 executes judgment, for example, based on a table stored in a storager which is provided in the controller 203. This table is created, for example, when the endoscope system 10 is shipped, or when the endoscope system 10 was previously used. This table includes driving currents which control the light sources 51V and 51B, and detection results corresponding to the driving currents. The judgment portion 205 executes judgment by comparing a detection result and the detection results in the table. For example, if abnormality occurs in at least one of the light sources 51V and 51B, light coupling/separating portion 217, light connector 73, light converter 75a, light guide path 71 and auxiliary light guide path 121, the detection result, which was detected by the detection main portion 335, differs from the detection result in the table. Thereby, abnormality is discovered, and the display 40 notifies the operator of the occurrence of abnormality. Responding to this, the operator connects the auxiliary light source module 110 to the light adapter 93 that is the auxiliary connector. Thereby, auxiliary light can be supplied to the irradiation module 75.

In this manner, the judgment portion 205 judges, based on the detection result of the detection unit 300, that a fault occurred in any one of the light sources, light coupler 57, light separator 81, light guide path 71, and the auxiliary light guide path 121 and light connector 73 which are provided in the endoscope 20. The judgment portion 205 have, for example, a hardware circuitry including ASIC.

Incidentally, the controller 203 may control the light sources 51V and 51B, based on the detection result.

The detection main portion 335 includes a photodiode or the like, which receives return light that was guided by the light guide member 71f.

The guide mouth portion 130 and light connector 73 are provided in the operation portion 23. Like the first embodiment, even when the light coupling/separating portion 217 became faulty and the light intensity decreased, the light intensity, which is in the decreased state, can be increased by the auxiliary light which is guided from the auxiliary guide light path 121 which is optically connected to the light guide path 71 by the light connector 73.

In the case where the endoscope 20 is of the wireless type, there is concern that the light intensity of illumination light decreases, even when the controller 213 or supply portion 215 became faulty. Even when the supply portion 215 is not faulty, if the residual amount of energy decreased, there is concern that the light intensity of illumination light decreases. Due to the use of the endoscope 20 in unexpected circumstances, or due to an external factor, there is concern that the residual amount of energy decreases more than expected, and the light intensity of illumination light decreases.

However, in the present embodiment, if abnormality is discovered by the determination result of the judgment portion 205, the auxiliary light source module 110 may be connected to the light adapter 93, and the auxiliary light may be guided to the light guide path 71. Thereby, in the state in which the light intensity decreased, the light intensity can be increased by the auxiliary light.

By the judgment of the judgment portion 205, monitoring can be executed for respective members and, as a result, the light intensity, which is in the decreased state, can be increased by the auxiliary light.

The light sources 51V and 51B emit laser beams. Thus, if abnormality occurs, there is concern that a high-output laser beam is emitted to the outside from the irradiation module 75. In this case, from the standpoint of the safety of eyes, there may be a fear of danger to the operator or patient. However, in the present embodiment, monitoring of abnormality is executed for the respective members, based on the detection result of return light. Thus, in this embodiment, attention can always be paid to abnormality by the monitoring.

When only the light source module 50 is used, the detection unit 300 is attached to the light adapter 93. Thus, monitoring can always be executed, and the above-described safety can be secured. If abnormality is discovered by the judgment result of the judgment portion 205, the detection unit 300 is detached from the light adapter 93, and the auxiliary light source module 110 is connected to the light adapter 93. Thereby, in the state in which the light intensity decreased, the light intensity can be increased by the auxiliary light.

In the present embodiment, the universal cord 25 is omitted. Thus, when the endoscope 20 is used, a free layout can be secured, without being restricted by the universal cord 25. The attitude and position of the endoscope 20 can be varied, without being pulled by the universal cord 25. In this manner, in the present embodiment, the convenience for use of the endoscope 20 can be improved.

In the meantime, when the judgment portion 205 has judged that the detection result is other than the normal value, if auxiliary light is supplied to the irradiation module 75, the light sources sly and 51B may be stopped, or the output of the light sources 51V and 51B may be lowered by the controller 213 controlling the light sources 51V and 51B.

When the judgment portion 205 has judged that the detection result is other than the normal value, the display 40 displays the occurrence of abnormality, and an alert is issued to the operator. However, the method of the alert is not limited to this. The operator may be notified by an alarm or the like. It should suffice if the abnormality is notified in such manners. Thus, the light source system 70 may include an alert portion which notifies the operator of abnormality. The alert portion issues an alert by, for example, sound. Incidentally, the alert portion includes the display 40.

The present invention is not limited directly to the above-described embodiments. At the stage of practicing the invention, the structural elements may be modified and embodied without departing from the spirit of the invention. Various inventions may be made by suitably combining a plurality of structural elements disclosed in the embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope light source system comprising:
    a plurality of light sources each configured to emit light-source light;
    a light coupler configured to couple the light-source light emitted from each of the plurality of light sources;
    an insertion section provided in an endoscope and optically connected to the plurality of light sources, the insertion section being configured to be inserted in a lumen;
    a light guide path optically connected to the light coupler, the light guide path being configured to guide the light-source light emitted from each of the plurality of light sources to the insertion section;
    an auxiliary light guide path configured to guide auxiliary light from an auxiliary light source separate from the plurality of light sources;
    a light connector provided on the light guide path, the light connector being configured to optically connect the auxiliary light guide path to the light guide path such that the auxiliary light is guided to the light guide path from the auxiliary light guide path; and
    a distal end of the insertion section optically connected to the light guide path, the distal end being configured to emit at least one of the light-source light guided by the light guide path and the auxiliary light guided by the light guide path, to an outside of the endoscope as illumination light, and to irradiate the illumination light to an illuminated part;
        wherein the light-source light and the auxiliary light enter the endoscope at different inlets and combine at the light connector within the endoscope.

2. The endoscope light source system according to claim 1, further comprising:
    a light separator configured to separate the light-source light coupled by the light coupler.

3. The endoscope light source system according to claim 2, wherein the light connector is provided between the light separator and the distal end, the light connector being provided closer to the distal end than to the light separator.

4. The endoscope light source system according to claim 3, further comprising a guide mouth connector detachably optically connected to the auxiliary light source, the guide mouth connector always being optically connected to the auxiliary light guide path, the guide mouth connector guiding the auxiliary light to the auxiliary light guide path when the guide mouth connector is connected to the auxiliary light source,
    wherein the light guide path includes a plurality of single optical fibers which are of mutually different systems, the plurality of single optical fibers being provided on at least a part of the light guide path and are configured to guide the light-source light emitted from the plurality of light sources,
    the auxiliary light guide includes a single auxiliary optical fiber which is a separate body from the plurality of single optical fibers, the single auxiliary optical fiber being provided on at least a part of the auxiliary light guide path and is configured to guide the auxiliary light, and
    the light connector optically connects the single auxiliary optical fiber to at least one of the plurality of single optical fibers.

5. The endoscope light source system according to claim 3, further comprising a guide mouth connector optically connected to the auxiliary light source and to the auxiliary light guide path, the guide mouth connector guiding the auxiliary light to the auxiliary light guide path,
wherein the guide mouth connector includes an auxiliary connecter optically connected to the auxiliary light source.

6. The endoscope light source system according to claim 5, wherein the guide mouth connector is provided in the endoscope and liquid-tightly seals the endoscope including the insertion section from an outer space portion.

7. The endoscope light source system according to claim 6, wherein the guide mouth connector includes a cap which caps the guide mouth connector, and
the cap is provided such that the auxiliary connecter is exposed by the cap being broken.

8. The endoscope light source system according to claim 3, further comprising a guide mouth connector optically connected to the auxiliary light source and to the auxiliary light guide path, the guide mouth connector guiding the auxiliary light to the auxiliary light guide path,
wherein the light guide path includes a universal cord optically connected to the light source and the guide mouth connector, the universal cord guiding the light-source light emitted from the plurality of light sources to the guide mouth connector.

9. The endoscope light source system according to claim 1, wherein the auxiliary light source is supplied with power, driven and controlled, independently from the plurality of light sources.

10. The endoscope light source system according to claim 9, wherein the auxiliary light source emits white light.

11. The endoscope light source system according to claim 9, wherein the auxiliary light source emits the auxiliary light having a wavelength which is equal to at least one wavelength of wavelengths of the light-source lights emitted from the plurality of light sources.

12. The endoscope light source system according to claim 3, further comprising a plurality of light converters disposed at the distal end, the plurality of light converters being configured to convert the light-source light and the auxiliary light to the illumination light.

13. The endoscope light source system according to claim 3, wherein the plurality of light sources emit the light-source lights having mutually optically different wavelengths.

14. The endoscope light source system according to claim 1, further comprising a guide mouth connector optically connected to the auxiliary light source and to the auxiliary light guide path, the guide mouth connector guiding the auxiliary light to the auxiliary light guide path,
wherein the plurality of light sources, the guide mouth connector and the light connector are provided in a rigid housing,
the insertion section includes a housing provided on at least a part of the insertion section and has flexibility, and
the light guide path, provided in the insertion section, is provided in an inside of the housing of the insertion section.

15. The endoscope light source system according to claim 1, further comprising a guide mouth connector optically connected to the auxiliary light source and to the auxiliary light guide path, the guide mouth connector guiding the auxiliary light to the auxiliary light guide path; and
a connector which detachably connects the plurality of light sources to the endoscope,
wherein the connector is provided closer to the light source than the guide mouth connector and the light connector.

16. The endoscope light source system according to claim 1, further comprising:
a light source having a housing, the plurality of light sources and the light combiner being disposed in the housing; and
the endoscope further comprising an operation portion provided at a proximal end of the insertion section, the light connector being disposed in the operation portion
wherein the light-source light and the auxiliary light enter the operation portion at the different inlets and combine at the light connector within the operation portion.

* * * * *